US012742149B2

(12) United States Patent
Yang et al.

(10) Patent No.: US 12,742,149 B2

(45) Date of Patent: Sep. 22, 2026

(54) **GENETICALLY ENGINEERED *ZYMOMONAS MOBILIS* ZM4 FOR PRODUCING PHB AND USES THEREOF**

(71) Applicant: Hubei University, Wuhan (CN)

(72) Inventors: Shihui Yang, Wuhan (CN); Qiaoning He, Wuhan (CN); Yang Li, Wuhan (CN)

( * ) Notice: Subject to any disclaimer, the term of this patent is extended or adjusted under 35 U.S.C. 154(b) by 884 days.

(21) Appl. No.: 18/146,506

(22) Filed: Dec. 27, 2022

(65) Prior Publication Data

US 2023/0407242 A1 Dec. 21, 2023

(51) Int. Cl.

| | |
|---|---|
| ***C12N 1/205*** | (2026.01) |
| ***C12P 7/06*** | (2006.01) |
| ***C12P 7/18*** | (2006.01) |
| ***C12R 1/01*** | (2006.01) |

(52) U.S. Cl.

CPC ................ *C12N 1/205* (2021.05); *C12P 7/06* (2013.01); *C12P 7/18* (2013.01); *C12R 2001/01* (2021.05)

(58) Field of Classification Search

CPC . C12N 15/00; C12N 1/205; C12P 7/14; C12P 7/06; Y02E 50/10

See application file for complete search history.

(56) References Cited

U.S. PATENT DOCUMENTS

2002/0146785 A1 10/2002 Mahishi et al.

FOREIGN PATENT DOCUMENTS

| | | | |
|---|---|---|---|
| CN | 104195158 | A | 12/2014 |
| CN | 108300732 | A | 7/2018 |
| CN | 110358720 | A | 10/2019 |
| CN | 112126609 | A | 12/2020 |
| WO | WO2013172928 | A1 | 11/2013 |

OTHER PUBLICATIONS

Shen et al., Microb Cell Fact, 2019; 18(162):1-11. (Year: 2019).*

* cited by examiner

*Primary Examiner* — Brian Gangle
*Assistant Examiner* — Lakia J Jackson-Tongue
(74) *Attorney, Agent, or Firm* — Nitin Kaushik

(57) ABSTRACT

The disclosure relates to a genetically engineered *Z. mobilis* ZM4 for producing PHB and uses thereof. A variety of strains capable of producing both PHB and ethanol that are constructed by integrating three codon-optimized essential genes for exogenous PUB biosynthesis, phaA, phaB and phaC, together with a tetracycline-inducible promoter Ptet into the genome of ZM4.

6 Claims, 16 Drawing Sheets

Specification includes a Sequence Listing.

SEQUENCE LISTING

```
Sequence total quantity: 68
SEQ ID NO: 1           moltype = DNA  length = 1770
FEATURE                Location/Qualifiers
source                 1..1770
                       mol_type = genomic DNA
                       organism = Cupriavidus necator
SEQUENCE: 1
atggccaccg gcaaaggtgc cgctgcctct acccaggaag gcaaaagcca acctttttaaa  60
gtcaccccgg gtccttttga tccggctacc tggttggaat ggtctcgcca gtggcaaggc  120
accgaaggca atggtcatgc tgccgctagc ggcattcctg gtttggatgc tttggccggc  180
gttaaaattg ctccggccca gttgggtgat atccagcaac gttatatgaa agatttctct  240
gccttgtggc aagctatggc cgaaggcaaa gctgaagcca ccggtccttt gcatgatcgt  300
cgctttgctg gtgatgcctg gcgcaccaat ttgccgtatc gttttgccgc tgccttttat  360
ttgttgaatg ctcgcgcctt gaccgaattg gctgatgccg tcgaagctga tgccaaaacc  420
cgtcagcgca ttcgttttgc catttctcaa tgggttgatg ccatgagccc ggctaatttt  480
cttgccacca atcctgaagc ccagcgtttg ttgattgaat ctggtggcga aagcttgcgc  540
gctggcgtcc gtaatatgat ggaagatttg acccgcggta aaatttctca aaccgatgaa  600
agcgcctttg aagttggccg taatgttgcc gtcaccgaag gtgctgttgt cttcgaaaat  660
gaatatttcc agttgttgca atataaaccg ttgaccgata aagtccatgc tcgccctttg  720
ttgatggttc cgccttgtat caataaatat tatatcttgg atttgcagcc tgaatctagc  780
ttggtccgcc atgttgtcga acaaggccat accgtctttt tggtctcttg gcgtaatccg  840
gatgcttcta tggccggtag cacctgggat gattatattg aacatgctgc cattcgcgct  900
attgaagttg cccgtgatat tagcggccag gataaaatca atgttttggg tttctgtgtc  960
ggtggcacca ttgtttctac cgctttggct gtcttggctg ctcgtggtga acatcctgct  1020
gctagcgtta ccttgttgac caccttgttg gattttgccg ataccggcat tttggatgtt  1080
tttgtcgatg aaggtcatgt tcaattgcgt gaagctacct tgggtggtgg tgctggtgct  1140
ccttgcgctt tgttgcgcgg tttggaattg gctaatacct ttagcttttt gcgtccgaat  1200
gatttggtct ggaattatgt tgtcgataat tatttgaaag gtaatacccc ggttcctttt  1260
gatttgttgt tttggaatgg cgatgccacc aatttgccgg gtccttggta ttgttggtat  1320
ttgcgccata cctatttgca gaatgaattg aaagtcccgg gcaaattgac cgtttgcggt  1380
gttcctgtcg atttggcctc tattgatgtc ccgacctata tttatggcag ccgtgaagat  1440
catattgttc cgtggaccgc tgcctatgct tctaccgcct tgttggctaa taaattgcgc  1500
```

```
tttgtcttgg gcgccagcgg tcatattgct ggtgttatta atccgcctgc caaaaataaa  1560
cgttctcatt ggaccaatga tgctttgccg gaaagccctc agcaatggtt ggctggcgcc  1620
attgaacatc atggtagctg gtggcctgat tggaccgcct ggttggctgg tcaagctggt  1680
gctaaacgtg ctgctcctgc caattatggc aatgctcgct atcgtgccat tgaaccggct  1740
cctggtcgtt atgttaaagc taaagcctaa                                    1770

SEQ ID NO: 2           moltype = DNA  length = 1182
FEATURE                Location/Qualifiers
source                 1..1182
                       mol_type = genomic DNA
                       organism = Cupriavidus necator
SEQUENCE: 2
atgaccgatg ttgtcattgt ctctgccgct cgtaccgccg ttggtaaatt tggtggcagc  60
ttggccaaaa ttccggctcc tgaattgggc gccgttgtca ttaaagccgc tttggaacgt  120
gctggtgtta aaccggaaca ggtctctgaa gttattatgg gccaagtctt gaccgctggt  180
agcggtcaga atcctgctcg tcaagccgct attaaagccg gtttgccggc tatggtccct  240
gccatgacca ttaataaagt ttgtggctct ggtttgaaag ccgtcatgtt ggccgctaat  300
gctattatgg ccggcgatgc tgaaattgtt gtcgctggtg gccaggaaaa tatgtctgcc  360
gctccgcatg ttttgcctgg cagccgtgat ggttttcgca tgggcgatgc caaattggtc  420
gataccatga ttgttgatgg tttgtgggat gtttataatc agtatcatat gggcatcacc  480
gctgaaaatg tcgccaaaga atatggtatt acccgcgaag cccaagatga atttgctgtt  540
ggtagccaga ataaagccga agccgctcaa aaagctggca aatttgatga agaaattgtc  600
ccggttttga ttcctcagcg taaaggtgat ccggttgcct ttaaaaccga tgaatttgtc  660
cgccaaggtg ctaccttgga ttctatgagc ggcttgaaac ctgcttttga taaagccggc  720
accgttaccg ccgctaatgc ctctggtttg aatgatggcg ccgctgccgt tgtcgttatg  780
agcgctgcca aagccaaaga attgggtttg accccgttgg ctaccattaa atcttatgct  840
aatgccggcg tcgatcctaa agttatgggc atgggtccgg ttcctgcttc taaacgtgcc  900
ttgagccgcg ctgaatggac cccgcaggat ttggatttga tggaaattaa tgaagccttt  960
gctgcccaag ctttggccgt ccatcagcaa atgggttggg atacctctaa agtcaatgtt  1020
aatggtggcg ctattgccat tggccatcct attggcgcca gcggttgtcg tattttggtt  1080
accttgttgc atgaaatgaa acgtcgcgat gccaaaaaag gcttggctag cttgtgcatt  1140
ggtggcggta tgggtgtcgc tttggccgtt gaacgcaaat aa                      1182

SEQ ID NO: 3           moltype = DNA  length = 741
FEATURE                Location/Qualifiers
source                 1..741
                       mol_type = genomic DNA
                       organism = Cupriavidus necator
SEQUENCE: 3
atgacccaac gtattgccta tgttaccggt ggcatgggtg gcattggcac cgccatttgt  60
cagcgtttgg ctaaagatgg ttttcgcgtt gtcgccggtt gcggcccgaa ttctcctcgt  120
cgcgaaaaat ggttggaaca gcaaaaagct ttgggctttg attttattgc ctctgaaggc  180
aatgttgctg attgggatag caccaaaacc gcctttgata aagttaaatc tgaagtcggc  240
gaagttgatg tcttgatcaa taatgctggt atcacccgcg atgttgtctt tcgtaaaatg  300
acccgcgccg attgggatgc tgtcattgat accaatttga ccagcttgtt caatgttacc  360
aaacaagtca tcgatggcat ggccgatcgt ggttggggcc gcattgttaa tatttctagc  420
gtcaatggtc agaaaggcca atttggtcag accaattatt ctaccgccaa agctggcttg  480
catggtttta ccatggcctt ggctcaagaa gtcgctacca aaggcgttac cgtcaatacc  540
gttagcccgg gttatattgc caccgatatg gtcaaagcta ttcgtcagga tgttttggat  600
aaaattgtcg ccaccattcc ggttaaacgc ttgggcttgc ctgaagaaat tgcctctatt  660
tgtgcttggt tgtctagcga agaatctggc tttagcaccg gtgctgattt tagcttgaat  720
ggtggcttgc atatgggtta a                                             741

SEQ ID NO: 4           moltype = DNA  length = 26
FEATURE                Location/Qualifiers
source                 1..26
                       mol_type = other DNA
                       organism = unidentified
SEQUENCE: 4
atcacagggt ctagaaggag gtcgaa                                        26

SEQ ID NO: 5           moltype = DNA  length = 727
FEATURE                Location/Qualifiers
source                 1..727
                       mol_type = other DNA
                       organism = unidentified
SEQUENCE: 5
ttaagaccca ctttcacatt taagttgttt ttctaatccg catatgatca attcaaggcc  60
gaataagaag gctggctctg caccttggtg atcaaataat tcgatagctt gtcgtaataa  120
tggcggcata ctatcagtag taggtgtttc cctttcttct ttagcgactt gatgctcttg  180
atcttccaat acgcaaccta aagtaaaatg ccccacagcg ctgagtgcat ataatgcatt  240
ctctagtgaa aaaccttgtt ggcataaaaa ggctaattga ttttcgagag tttcatactg  300
tttttctgta ggccgtgtac ctaaatgtac ttttgctcca tcgcgatgac ttagtaaagc  360
acatctaaaa cttttagcgt tattacgtaa aaaatcttgc cagctttccc cttctaaagg  420
gcaaaagtga gtatggtgcc tatctaacat ctcaatggct aaggcgtcga gcaaagcccg  480
cttatttttt acatgccaat acaatgtagg ctgctctaca cctagcttct gggcgagttt  540
acgggttgtt aaaccttcga ttccgacctc attaagcagc tctaatgcgc tgttaatcac  600
tttactttta tctaatctgg acatcattaa ttcctaattt ttgttgacac tctatcgttg  660
atagagttat tttaccactc cctatcagtg atagagaaaa gtattcaaat gatctaaaga  720
```

-continued

```
ggagaaa                                                          727

SEQ ID NO: 6           moltype = DNA  length = 305
FEATURE                Location/Qualifiers
source                 1..305
                       mol_type = other DNA
                       organism = unidentified
SEQUENCE: 6
gttcgatcaa caacccgaat cctatcgtaa tgatgttttg cccgatcagc ctcaatcgac  60
aattttacgc gtttcgatcg aagcagggac gacaattggc tgggaacggt atactggaat  120
aaatggtctt cgttatggta ttgatgtttt tggtgcatcg gccccggcga atgatctata  180
tgctcatttc ggcttgaccg cagtcggcat cacgaacaag gtgttggccg cgatcgccgg  240
taagtcggca cgttaaaaaa tagctatgga atatagtagc tacttaataa gttaggagaa  300
taaac                                                            305

SEQ ID NO: 7           moltype = DNA  length = 4365
FEATURE                Location/Qualifiers
source                 1..4365
                       mol_type = other DNA
                       organism = synthetic construct
SEQUENCE: 7
ttaagaccca ctttcacatt taagttgttt ttctaatccg catatgatca attcaaggcc  60
gaataagaag gctggctctg caccttggtg atcaaataat tcgatagctt gtcgtaataa  120
tggcggcata ctatcagtag taggtgtttc cctttcttct ttagcgactt gatgctcttg  180
atcttccaat acgcaaccta aagtaaaatg ccccacagcg ctgagtgcat ataatgcatt  240
ctctagtgaa aaaccttgtt ggcataaaaa ggctaattga ttttcgagag tttcatactg  300
tttttctgta ggccgtgtac ctaaatgtac ttttgctcca tcgcgatgac ttagtaaagc  360
acatctaaaa cttttagcgt tattacgtaa aaaatcttgc cagctttccc cttctaaagg  420
gcaaaagtga gtatggtgcc tatctaacat ctcaatggct aaggcgtcga gcaaagcccg  480
cttatttttt acatgccaat acaatgtagg ctgctctaca cctagcttct gggcgagttt  540
acgggttgtt aaaccttcga ttccgacctc attaagcagc tctaatgcgc tgttaatcac  600
tttactttta tctaatctgg acatatggcc accggcaaag gtgccgctgc ctctacccag  660
gaaggcaaaa gccaaccttt taaagtcacc ccgggtcctt ttgatccggc tacctggttg  720
gaatggtctc gccagtggca aggcaccgaa ggcaatggtc atgctgccgc tagcggcatt  780
cctggtttgg atgctttggc cggcgttaaa attgctccgg cccagttggg tgatatccag  840
caacgttata tgaaagattt ctctgccttg tggcaagcta tggccgaagg caaagctgaa  900
gccaccggtc ctttgcatga tcgtcgcttt gctggtgatg cctggcgcac caatttgccg  960
tatcgttttg ccgctgcctt ttatttgttg aatgctcgcg ccttgaccga attggctgat  1020
gccgtcgaag ctgatgccaa aacccgtcag cgcattcgtt ttgccatttc tcaatgggtt  1080
gatgccatga gcccggctaa ttttcttgcc accaatcctg aagcccagcg tttgttgatt  1140
gaatctggtg gcgaaagctt gcgcgctggc gtccgtaata tgatggaaga tttgacccgc  1200
ggtaaaattt ctcaaaccga tgaaagcgcc tttgaagttg gccgtaatgt tgccgtcacc  1260
gaaggtgctg ttgtcttcga aaatgaatat ttccagttgt tgcaatataa accgttgacc  1320
gataaagtcc atgctcgccc tttgttgatg gttccgcctt gtatcaataa atattatatc  1380
ttggatttgc agcctgaatc tagcttggtc cgccatgttg tcgaacaagg ccataccgtc  1440
tttttggtct cttggcgtaa tccggatgct tctatggccg gtagcacctg ggatgattat  1500
attgaacatg ctgccattcg cgctattgaa gttgcccgtg atattagcgg ccaggataaa  1560
atcaatgttt tgggtttctg tgtcggtggc accattgttt ctaccgcttt ggctgtcttg  1620
gctgctcgtg gtgaacatcc tgctgctagc gttaccttgt tgaccacctt gttggatttt  1680
gccgataccg gcattttgga tgtttttgtc gatgaaggtc atgttcaatt gcgtgaagct  1740
accttgggtg gtggtgctgg tgctccttgc gctttgttgc gcggtttgga attggctaat  1800
acctttagct tttgcgtcc gaatgatttg gtctggaatt atgttgtcga taattatttg  1860
aaaggtaata ccccggttcc ttttgatttg ttgttttgga atggcgatgc caccaatttg  1920
ccgggtcctt ggtattgttg gtatttgcgc catacctatt tgcagaatga attgaaagtc  1980
ccgggcaaat tgaccgtttg cggtgttcct gtcgatttgg cctctattga tgtcccgacc  2040
tatatttatg gcagccgtga agatcatatt gttccgtgga ccgctgccta tgcttctacc  2100
gccttgttgg ctaataaatt gcgctttgtc ttgggcgcca gcggtcatat tgctggtgtt  2160
attaatccgc ctgccaaaaa taaacgttct cattggacca atgatgcttt gccggaaagc  2220
cctcagcaat ggttggctgg cgccattgaa catcatggta gctggtggcc tgattggacc  2280
gcctggttgg ctggtcaagc tggtgctaaa cgtgctgctc ctgccaatta tggcaatgct  2340
cgctatcgtg ccattgaacc ggctcctggt cgttatgtta aagctaaagc ctaaccataa  2400
tctagagaaa gtaagcacat gaccgatgtt gtcattgtct ctgccgctcg taccgccgtt  2460
ggtaaatttg gtggcagctt ggccaaaatt ccggctcctg aattgggcgc cgttgtcatt  2520
aaagccgctt tggaacgtgc tggtgttaaa ccggaacagg tctctgaagt tattatgggc  2580
caagtcttga ccgctggtag cggtcagaat cctgctcgtc aagccgctat taaagccggt  2640
ttgccggcta tggtccctgc catgaccatt aataaagttt gtggctctgg tttgaaagcc  2700
gtcatgttgg ccgctaatgc tattatggcc ggcgatgctg aaattgttgt cgctggtggc  2760
caggaaaata tgtctgccgc tccgcatgtt ttgcctggca gccgtgatgg ttttcgcatg  2820
ggcgatgcca aattggtcga taccatgatt gttgatggtt tgtgggatgt ttataatcag  2880
tatcatatgg gcatcaccgc tgaaaatgtc gccaaagaat atggtattac ccgcgaagcc  2940
caagatgaat ttgctgttgg tagccagaat aaagccgaag ccgctcaaaa agctggcaaa  3000
tttgatgaag aaattgtccc ggttttgatt cctcagcgta aaggtgatcc ggttgccttt  3060
aaaaccgatg aatttgtccg ccaaggtgct accttggatt ctatgagcgg cttgaaacct  3120
gcttttgata aagccggcac cgttaccgcc gctaatgcct ctggtttgaa tgatggcgcc  3180
gctgccgttg tcgttatgag cgctgccaaa gccaaagaat tgggtttgac cccgttggct  3240
accattaaat cttatgctaa tgccggcgtc gatcctaaag ttatgggcat gggtccggtt  3300
cctgcttcta aacgtgcctt gagccgcgct gaatggaccc cgcaggattt ggatttgatg  3360
gaaattaatg aagcctttgc tgcccaagct ttggccgtcc atcagcaaat gggttgggat  3420
acctctaaag tcaatgttaa tggtggcgct attgccattg gccatcctat tggcgccagc  3480
```

-continued

```
ggttgtcgta ttttggttac cttgttgcat gaaatgaaac gtcgcgatgc caaaaaaggc  3540
ttggctagct tgtgcattgg tggcggtatg ggtgtcgctt tggccgttga acgcaaataa  3600
ccataatcta gagaaagtaa gcacatgacc caacgtattg cctatgttac cggtggcatg  3660
ggtggcattg gcaccgccat ttgtcagcgt ttggctaaag atggttttcg cgttgtcgcc  3720
ggttgcggcc cgaattctcc tcgtcgcgaa aaatggttgg aacagcaaaa agctttgggc  3780
tttgatttta ttgcctctga aggcaatgtt gctgattggg atagcaccaa aaccgccttt  3840
gataaagtta aatctgaagt cggcgaagtt gatgtcttga tcaataatgc tggtatcacc  3900
cgcgatgttg tctttcgtaa aatgacccgc gccgattggg atgctgtcat tgataccaat  3960
ttgaccagct tgttcaatgt taccaaacaa gtcatcgatg gcatggccga tcgtggttgg  4020
ggccgcattg ttaatatttc tagcgtcaat ggtcagaaag gccaatttgg tcagaccaat  4080
tattctaccg ccaaagctgg cttgcatggt tttaccatgg ccttggctca agaagtcgct  4140
accaaaggcg ttaccgtcaa taccgttagc ccgggttata ttgccaccga tatggtcaaa  4200
gctattcgtc aggatgtttt ggataaaatt gtcgccacca ttccggttaa acgcttgggc  4260
ttgcctgaag aaattgcctc tatttgtgct tggttgtcta gcgaagaatc tggctttagc  4320
accggtgctg attttagctt gaatggtggc ttgcatatgg gttaa                   4365

SEQ ID NO: 8            moltype = DNA  length = 30
FEATURE                 Location/Qualifiers
source                  1..30
                        mol_type = other DNA
                        organism = synthetic construct
SEQUENCE: 8
gatctcccgg atccatggcc accggcaaag                                    30

SEQ ID NO: 9            moltype = DNA  length = 50
FEATURE                 Location/Qualifiers
source                  1..50
                        mol_type = other DNA
                        organism = synthetic construct
SEQUENCE: 9
cttactttct ctagattatg gttaggcttt agctttaaca taacgaccag              50

SEQ ID NO: 10           moltype = DNA  length = 49
FEATURE                 Location/Qualifiers
source                  1..49
                        mol_type = other DNA
                        organism = synthetic construct
SEQUENCE: 10
ccataatcta gagaaagtaa gcacatgacc gatgttgtca ttgtctctg               49

SEQ ID NO: 11           moltype = DNA  length = 47
FEATURE                 Location/Qualifiers
source                  1..47
                        mol_type = other DNA
                        organism = synthetic construct
SEQUENCE: 11
gtgcttactt tctctagatt atggttattt gcgttcaacg gccaaag                 47

SEQ ID NO: 12           moltype = DNA  length = 39
FEATURE                 Location/Qualifiers
source                  1..39
                        mol_type = other DNA
                        organism = synthetic construct
SEQUENCE: 12
ctagagaaag taagcacatg acccaacgta ttgcctatc                          39

SEQ ID NO: 13           moltype = DNA  length = 38
FEATURE                 Location/Qualifiers
source                  1..38
                        mol_type = other DNA
                        organism = synthetic construct
SEQUENCE: 13
ggccgctact agtttaaccc atatgcaagc caccattc                           38

SEQ ID NO: 14           moltype = DNA  length = 42
FEATURE                 Location/Qualifiers
source                  1..42
                        mol_type = other DNA
                        organism = synthetic construct
SEQUENCE: 14
cggccgcttc tagagttaag acccactttc acatttaagt tg                      42

SEQ ID NO: 15           moltype = DNA  length = 26
FEATURE                 Location/Qualifiers
source                  1..26
                        mol_type = other DNA
                        organism = synthetic construct
SEQUENCE: 15
gggagatcct ttctcctctt tagatc                                        26
```

```
SEQ ID NO: 16          moltype = DNA  length = 22
FEATURE                Location/Qualifiers
source                 1..22
                       mol_type = other DNA
                       organism = synthetic construct
SEQUENCE: 16
ggcaaagcca ccctattttt ag                                            22

SEQ ID NO: 17          moltype = DNA  length = 20
FEATURE                Location/Qualifiers
source                 1..20
                       mol_type = other DNA
                       organism = synthetic construct
SEQUENCE: 17
cacttcactg acaccctcat                                               20

SEQ ID NO: 18          moltype = DNA  length = 39
FEATURE                Location/Qualifiers
source                 1..39
                       mol_type = other DNA
                       organism = unidentified
SEQUENCE: 18
cttaataagt taggagaata aacatggcca ccggcaaag                          39

SEQ ID NO: 19          moltype = DNA  length = 36
FEATURE                Location/Qualifiers
source                 1..36
                       mol_type = other DNA
                       organism = synthetic construct
SEQUENCE: 19
gaaagcgtcc agcaaaatac gccttctatt gatgaa                             36

SEQ ID NO: 20          moltype = DNA  length = 36
FEATURE                Location/Qualifiers
source                 1..36
                       mol_type = other DNA
                       organism = synthetic construct
SEQUENCE: 20
gaacttcatc aatagaaggc gtattttgct ggacgc                             36

SEQ ID NO: 21          moltype = DNA  length = 35
FEATURE                Location/Qualifiers
source                 1..35
                       mol_type = other DNA
                       organism = synthetic construct
SEQUENCE: 21
caccagctca ccgtctgctt tttgccgaca aagcg                              35

SEQ ID NO: 22          moltype = DNA  length = 37
FEATURE                Location/Qualifiers
source                 1..37
                       mol_type = other DNA
                       organism = synthetic construct
SEQUENCE: 22
tcacgcccga cgccagacgg gattagaaat tttgtcg                            37

SEQ ID NO: 23          moltype = DNA  length = 52
FEATURE                Location/Qualifiers
source                 1..52
                       mol_type = other DNA
                       organism = synthetic construct
SEQUENCE: 23
ggcgtcgggc gtgattaaga cccactttca catttaagtt gtttttctaa tc           52

SEQ ID NO: 24          moltype = DNA  length = 43
FEATURE                Location/Qualifiers
source                 1..43
                       mol_type = other DNA
                       organism = synthetic construct
SEQUENCE: 24
cgtctatctg aatatttaac gattaaccca tatgcaagcc acc                     43

SEQ ID NO: 25          moltype = DNA  length = 47
FEATURE                Location/Qualifiers
source                 1..47
                       mol_type = other DNA
                       organism = synthetic construct
SEQUENCE: 25
```

```
tcgttaaata ttcagataga cggagataat aaacgggaga gaggtcg             47

SEQ ID NO: 26          moltype = DNA  length = 33
FEATURE                Location/Qualifiers
source                 1..33
                       mol_type = other DNA
                       organism = synthetic construct
SEQUENCE: 26
gctcgagatc tgatatcact caacagatca acc                            33

SEQ ID NO: 27          moltype = DNA  length = 40
FEATURE                Location/Qualifiers
source                 1..40
                       mol_type = other DNA
                       organism = synthetic construct
SEQUENCE: 27
ggcgtcgggc gtgagttcga tcaacaaccc gaatcctatc                     40

SEQ ID NO: 28          moltype = DNA  length = 37
FEATURE                Location/Qualifiers
source                 1..37
                       mol_type = other DNA
                       organism = synthetic construct
SEQUENCE: 28
gtgatatcag atctcgagct cggtacccgg gtttgac                        37

SEQ ID NO: 29          moltype = DNA  length = 36
FEATURE                Location/Qualifiers
source                 1..36
                       mol_type = other DNA
                       organism = synthetic construct
SEQUENCE: 29
gacggtgagc tggtgacctg ccttatctct ttcccc                         36

SEQ ID NO: 30          moltype = DNA  length = 26
FEATURE                Location/Qualifiers
source                 1..26
                       mol_type = other DNA
                       organism = synthetic construct
SEQUENCE: 30
tgccagcttc tgttggagaa aacagg                                    26

SEQ ID NO: 31          moltype = DNA  length = 17
FEATURE                Location/Qualifiers
source                 1..17
                       mol_type = other DNA
                       organism = synthetic construct
SEQUENCE: 31
cgcaagccaa gctgcgt                                              17

SEQ ID NO: 32          moltype = DNA  length = 501
FEATURE                Location/Qualifiers
source                 1..501
                       mol_type = other DNA
                       organism = synthetic construct
SEQUENCE: 32
tcacgcccga cgccagacgg gattagaaat tttgtcgata aacgcgccgt gacgcaataa  60
ttcttgtggg ctggcctcgt ggggtcttgg ttgtcttttg accttttttat tacgaggtag  120
accggaaacc gtgttcgggg cagacaagcg tccatcggat gggccgttat tgtcatccaa  180
ggccataccg atttgccgtc cgcctgtcag ttcaacataa agctgtgcca gcaattcggc  240
atcgagcaag gcgccatgtt tgacgcgatg gctgcggtca ataccgtagc gggtacataa  300
tgcgtcaagg gtatgtttgg caccgggatg tttgccgcgc gcaatcgcca aggtatcgac  360
cattcgggtc atacaaatgg tcggaaggcc gcatttatcc aattcgtaat tcaaaaagcc  420
gaaatcgaag gccgcattat gggcgaccaa aggcgacaat ttgataaagg aaagcagttc  480
ttgcgctttg tcggcaaaaa g                                         501

SEQ ID NO: 33          moltype = DNA  length = 500
FEATURE                Location/Qualifiers
source                 1..500
                       mol_type = other DNA
                       organism = synthetic construct
SEQUENCE: 33
caacagatca accggcaatt tatccacggc atcaaattcg atcggttctt tcaggcggac  60
aaaaaagccg gagacttttt tcaggctgtc gagcttgcca tgtggtatcg caataccatg  120
accaaaacct gtcgaaccga gcgtttctct ttcatgtaac cgttcggcga taaccttggg  180
gttaattaga aattctcgcc cagcccattg ggcaacctgc tggaagagtg tttttttgtt  240
agaaggattg aaattcacct caatcctgtc cggcgcgatt atatcggcca gttcattcat  300
gttttttcgc ctttatatgc ccacgattgc aaagatcgca gcatcagaca ttttctgaaa  360
gacacagcct ttcagaaaat aaagtcaaaa ttctagcaat attccttccg gaaacggggg  420
```

```
agaggggtcg ataattctct tgaaaagagg gagcgacctc tctcccgttt attatctccg  480
tctatctgaa tatttaacga                                              500

SEQ ID NO: 34          moltype = DNA  length = 42
FEATURE                Location/Qualifiers
source                 1..42
                       mol_type = other DNA
                       organism = synthetic construct
SEQUENCE: 34
gttaaaaaga ggagaaagga tctcccatgg ccaccggcaa ag                     42

SEQ ID NO: 35          moltype = DNA  length = 39
FEATURE                Location/Qualifiers
source                 1..39
                       mol_type = other DNA
                       organism = synthetic construct
SEQUENCE: 35
tcctttctcc tctttttaac ataagcgaaa ttgttcgcg                         39

SEQ ID NO: 36          moltype = DNA  length = 24
FEATURE                Location/Qualifiers
source                 1..24
                       mol_type = other DNA
                       organism = synthetic construct
SEQUENCE: 36
atgacaaata ccgtttcgac gatg                                         24

SEQ ID NO: 37          moltype = DNA  length = 45
FEATURE                Location/Qualifiers
source                 1..45
                       mol_type = other DNA
                       organism = synthetic construct
SEQUENCE: 37
gagatccttt ctcctctttt cagtcatacc aagttactcc atcac                  45

SEQ ID NO: 38          moltype = DNA  length = 38
FEATURE                Location/Qualifiers
source                 1..38
                       mol_type = other DNA
                       organism = synthetic construct
SEQUENCE: 38
aaagaggaga aaggatctcc catggccacc ggcaaagg                          38

SEQ ID NO: 39          moltype = DNA  length = 1380
FEATURE                Location/Qualifiers
source                 1..1380
                       mol_type = genomic DNA
                       organism = Saccharomyces cerevisiae
SEQUENCE: 39
atggaacata gcgttattga accgaccgtt ccgatgccga tgccggctat gtttgatgcg  60
ccgtctggta tttttgatag cttggatgat gcggttcagg cggccgttta tgcgcaacaa  120
cagttaaatt ctgttgaatt gcgtcagcag gttattaaag ctattcgtgt tgccggtgaa  180
cgttatgcgc aggttttggc tgaaatggct gttgccgaaa ccggtatggg tcgtgtcgtt  240
gataaatata ttaaaaatgt ttctcaagct cgtcatacgc cgggtattga atgtttgtct  300
gccgaagttt tgaccggtga taatggtttg accttgattg aaaatgctcc ttggggtgtt  360
gttgcctctg ttaccccgtc taccaatccg gctgccaccg ttattaataa tgccatttct  420
atgatcgccg ccggtaattc tgttgttttt gccccgcatc cgtctgccaa aaatgttagc  480
ttgcgtacca tttctctttt gaataaagcc attgttgcga ccggcggtcc ggaaaatttg  540
ttggtttctg tttctgatcc gaatattgaa accgcccaac gtttatttcg ttatccgggt  600
attggcctgt tggttgttac gggtggtgaa gccgttgttg aagctgcccg tcgtcatacc  660
gataaacgtt tgattgccgc cggcgccggt aatcctcctg ttgttgttga tgaaacggcg  720
gatattccga aagccgcccg tgctattgtt aaaggtgcct cttttgataa taatatcatc  780
tgcgccgatg aaaaagtttt gattgttgtt gatagcgttg ccgatgcctt gttggccgaa  840
atgcagcgta atcatgctgt tttgttgacg ccggcccaga ccgaacagtt gttgcctgct  900
ttgttgtctg atattgatga acagggtaaa ggtcgtgtta atcgtgatta tgttggtcgt  960
gatgccacca aattggccga agccattggt ttagaagtta atgaatatac gcgtttgttg  1020
ttggccgaaa ccgatgccag ccatccgttt gctgttaccg aattgatgat gccggttttg  1080
ccggttgttc gtgttaaatc tgttgatgat gccattgcct tggccctgaa attggaaaat  1140
ggttgtcgcc ataccgccgc catgcattct accaatattc gtaatttgaa tcgtatggct  1200
aatgccatta atacctccat ttttgttaaa aatggtccgt gtattgccgg tttgggtttg  1260
ggtggtgaag gttggacctc tatgaccatt tctaccccga ccggtgaagg tgtcacctct  1320
gctcgtacgt ttgttcgttt gcgtcgttgt gttttggttg atatgtttcg tattgcttaa  1380

SEQ ID NO: 40          moltype = DNA  length = 1047
FEATURE                Location/Qualifiers
source                 1..1047
                       mol_type = genomic DNA
                       organism = Saccharomyces cerevisiae
SEQUENCE: 40
```

-continued

```
atgagcattc cggaaaccca gaaagcgatt attttttatg aaagcaatgg caaattggaa  60
cataaagata ttccggttcc gaaaccgaaa ccgaatgaat tgttgattaa tgttaaatat  120
tctggtgttt gtcataccga tttgcatgcc tggcatggtg attggccgtt gcctaccaaa  180
ttgcctttag ttggtggtca tgaaggtgcc ggtgttgttg ttggtatggg tgaaaatgtt  240
aaaggttgga aaattggtga ttatgccggt attaaatggt tgaatggttc ttgtatggct  300
tgtgaatatt gtgaattggg taatgaatct aattgcccgc atgccgattt gtctggttat  360
acgcatgatg gttcttttca ggaatatgcc accgctgatg ccgttcaggc tgctcatatt  420
ccgcagggta ccgatttggc cgaagtcgct cctattttgt gtgccggtat tacggtctat  480
aaagccttga aatctgccaa tttgcgtgcc ggtcattggg ccgctatttc tggtgctgcc  540
ggtggtttgg gttctttggc tgttcagtat gctaaagcta tgggttatcg cgttcttggt  600
attgatggtg gtccgggtaa agaagaattg tttacgtctt tgggtggtga agtttttatt  660
gattttacga aagaaaaaga tatcgtttcc gctgttgtta aagccacgaa tggtggtgct  720
catggtatta ttaatgttag cgtttctgaa gccgctattg aagcttctac ccgttattgt  780
cgtgccaatg gtaccgttgt tttggttggt ttgccggctg gtgctaaatg ttcttctgat  840
gtttttaatc atgttgtcaa aagcatctct atcgtcggct cttatgttgg taatcgtgct  900
gatacgcgtg aagccttgga ttttttttgct cgtggtttgg ttaaatctcc cattaaagtt  960
gttggtttat cttctttgcc ggaaatttat gaaaaaaatgg aaaaaggtca gattgccggt  1020
cgttatgttg ttgatacctc taaataa                                       1047

SEQ ID NO: 41          moltype = DNA  length = 1434
FEATURE                Location/Qualifiers
source                 1..1434
                       mol_type = genomic DNA
                       organism = Zymomonas mobilis
SEQUENCE: 41
ctatcgaaag gcaaatttct ttctcgccga gcctgtgagc gaagcgagca gcgccgagag  60
attaacgggc ggtgggcttt gagaaggatc gctatcaggc tttcgattat aaatagcgtc  120
tacactgtct gcggcaggag cagtgcagtc cttatcttct tctttggttt ttagttttgt  180
atggtcgcta ttagataaat aagtataaca ggatagagta taagaattga actcgcgttg  240
attgtccgag atttggggct tttttgaggt atcctccttg gaggttttag aagatatttt  300
aacctcttcc tgatcagtct gtgctgcctt cttagcctga gcttcttgtt cccgttgttc  360
cgcccgctcg atagatttgg cgagctgtat gagcgaatcc gttagctctg ttggttcttt  420
attgtccgat atcgctttga cgaaatcttc gggaggcaag ctttcaacga tagccttggt  480
ttcggctttg tccgcctctt gggcgtggtc aatatcgtca ggaataggcg cattcctccg  540
gcgcatgacg cgctcgaaaa cctgtctggc caactctggc caatccttgg gagacaagaa  600
gccgtaggcg ttactggtct gcttacggcg ggggcctttg ccatccgccg tgatcttgat  660
tgatcggcgt atccagcgga tgaagcctaa atcctgtaat tgccgcagta atttgacgac  720
cgtcgcacgg gcatagccga cacgatcgca tattgtgtcg agggtcggct ctaaccgacc  780
agttttaaag tcgaccatcc gaaacagcat ctttagaagg cgaacggcct tatcgcttaa  840
gcccttggtt ttgatcgaat attgatcgac cgcttccaga taggcaccga tctcttgcgg  900
attgaccggc ttccagaccg acttctcgcg ttcgccaacc tcataagaat cccgatgcac  960
aggatcagga gtttgacggc gggttttata gcgaatggct cgttcgagag ggtctctacg  1020
tctcgcaata gctgttttgc gagcaatatc tgcagcggtt tcaggatcac atccgctaga  1080
taccatctga tcaaaatatt ctatctcgtc gaaatctgat gcggaggctg taacctcact  1140
attggtattt gaggccggaa tttcgggatg agcgctattg gccaaggaca ttgatttaga  1200
gaatgcacgg tctattttat gctgttctgc ggctcgatct gccataatct ttgcgctatc  1260
atatggcata cccgtttcaa ccaacatggc tcgataagtg ccacgcttga aacggcctag  1320
cctgtcgata aaaggactgg ttacgggcgt cgtttgttca aaagacgcag agacaggctc  1380
taaagaaaag acagaggcat ccgagagtgt cgctgaagag gaagaggcag tcat         1434

SEQ ID NO: 42          moltype = DNA  length = 46
FEATURE                Location/Qualifiers
source                 1..46
                       mol_type = other DNA
                       organism = synthetic construct
SEQUENCE: 42
ttccgtagtg agtactgaat ctatcgaaag gcaaatttct ttctcg                  46

SEQ ID NO: 43          moltype = DNA  length = 35
FEATURE                Location/Qualifiers
source                 1..35
                       mol_type = other DNA
                       organism = synthetic construct
SEQUENCE: 43
agaagcggcc gcgaattcag tcagaaccgg cgccc                              35

SEQ ID NO: 44          moltype = DNA  length = 16
FEATURE                Location/Qualifiers
source                 1..16
                       mol_type = other DNA
                       organism = synthetic construct
SEQUENCE: 44
ctgaattcgc ggccgc                                                   16

SEQ ID NO: 45          moltype = DNA  length = 24
FEATURE                Location/Qualifiers
source                 1..24
                       mol_type = other DNA
                       organism = synthetic construct
```

```
SEQUENCE: 45
attcagtact cactacggaa ttgc                                          24

SEQ ID NO: 46          moltype = DNA  length = 17
FEATURE                Location/Qualifiers
source                 1..17
                       mol_type = other DNA
                       organism = synthetic construct
SEQUENCE: 46
cggctctaac cgaccag                                                  17

SEQ ID NO: 47          moltype = DNA  length = 2453
FEATURE                Location/Qualifiers
source                 1..2453
                       mol_type = other DNA
                       organism = synthetic construct
SEQUENCE: 47
atggaacata gcgttattga accgaccgtt ccgatgccga tgccggctat gtttgatgcg  60
ccgtctggta tttttgatag cttggatgat gcggttcagg cggccgttta tgcgcaacaa  120
cagttaaatt ctgttgaatt gcgtcagcag gttattaaag ctattcgtgt tgccggtgaa  180
cgttatgcgc aggttttggc tgaaatggct gttgccgaaa ccggtatggg tcgtgtcgtt  240
gataaatata ttaaaaatgt ttctcaagct cgtcatacgc cgggtattga atgtttgtct  300
gccgaagttt tgaccggtga taatggtttg accttgattg aaaatgctcc ttggggtgtt  360
gttgcctctg ttaccccgtc taccaatccg gctgccaccg ttattaataa tgccatttct  420
atgatcgccg ccggtaattc tgttgttttt gccccgcatc cgtctgccaa aaatgttagc  480
ttgcgtacca tttctctttt gaataaagcc attgttgcga ccggcggtcc ggaaaatttg  540
ttggtttctg tttctgatcc gaatattgaa accgcccaac gtttatttcg ttatccgggt  600
attggcctgt tggttgttac gggtggtgaa gccgttgttg aagctgcccg tcgtcatacc  660
gataaacgtt tgattgccgc cggcgccggt aatcctcctg ttgttgttga tgaaacggcg  720
gatattccga aagccgcccg tgctattgtt aaaggtgcct cttttgataa taatatcatc  780
tgcgccgatg aaaaagtttt gattgttgtt gatagcgttg ccgatgcctt gttggccgaa  840
atgcagcgta atcatgctgt tttgttgacg ccggcccaga ccgaacagtt gttgcctgct  900
ttgttgtctg atattgatga acagggtaaa ggtcgtgtta atcgtgatta tgttggtcgt  960
gatgccacca aattggccga agccattggt ttagaagtta atgaatatac gcgtttgttg  1020
ttggccgaaa ccgatgccag ccatccgttt gctgttaccg aattgatgat gccggttttg  1080
ccggttgttc gtgttaaatc tgttgatgat gccattgcct tggccctgaa attggaaaat  1140
ggttgtcgcc ataccgccgc catgcattct accaatattc gtaatttgaa tcgtatggct  1200
aatgccatta atacctccat ttttgttaaa aatggtccgt gtattgccgg tttgggtttg  1260
ggtggtgaag gttggacctc tatgaccatt tctaccccga ccggtgaagg tgtcacctct  1320
gctcgtacgt ttgttcgttt gcgtcgttgt gttttggttg atatgtttcg tattgcttaa  1380
atcacagggt ctagaaggag gtcgaaatga gcattccgga aacccagaaa gcgattattt  1440
tttatgaaag caatggcaaa ttggaacata aagatattcc ggttccgaaa ccgaaaccga  1500
atgaattgtt gattaatgtt aaatattctg gtgtttgtca taccgatttg catgcctggc  1560
atggtgattg gccgttgcct accaaattgc ctttagttgg tggtcatgaa ggtgccggtg  1620
ttgttgttgg tatgggtgaa aatgttaaag gttggaaaat tggtgattat gccggtatta  1680
aatggttgaa tggttcttgt atggcttgtg aatattgtga attgggtaat gaatctaatt  1740
gcccgcatgc cgatttgtct ggttatacgc atgatggttc ttttcaggaa tatgccaccg  1800
ctgatgccgt tcaggctgct catattccgc agggtaccga tttggccgaa gtcgctccta  1860
ttttgtgtgc cggtattacg gtctataaag ccttgaaatc tgccaatttg cgtgccggtc  1920
attgggccgc tatttctggt gctgccggtg gtttgggttc tttggctgtt cagtatgcta  1980
aagctatggg ttatcgcgtt cttggtattg atggtggtcc gggtaaagaa gaattgttta  2040
cgtctttggg tggtgaagtt tttattgatt ttacgaaaga aaaagatatc gtttccgctg  2100
ttgttaaagc cacgaatggt ggtgctcatg gtattattaa tgttagcgtt tctgaagccg  2160
ctattgaagc ttctacccgt tattgtcgtg ccaatggtac cgttgttttg gttggtttgc  2220
cggctggtgc taaatgttct tctgatgttt ttaatcatgt tgtcaaaagc atctctatcg  2280
tcggctctta tgttggtaat cgtgctgata cgcgtgaagc cttggatttt tttgctcgtg  2340
gtttggttaa atctcccatt aaagttgttg gtttatcttc tttgccggaa atttatgaaa  2400
aaatggaaaa aggtcagatt gccggtcgtt atgttgttga tacctctaaa taa         2453

SEQ ID NO: 48          moltype = DNA  length = 19
FEATURE                Location/Qualifiers
source                 1..19
                       mol_type = other DNA
                       organism = synthetic construct
SEQUENCE: 48
cgtcccatag atctcgagc                                                19

SEQ ID NO: 49          moltype = DNA  length = 26
FEATURE                Location/Qualifiers
source                 1..26
                       mol_type = other DNA
                       organism = synthetic construct
SEQUENCE: 49
gatgtttaac tcctgaatta agccgc                                        26

SEQ ID NO: 50          moltype = DNA  length = 27
FEATURE                Location/Qualifiers
source                 1..27
                       mol_type = other DNA
```

```
                        organism = synthetic construct
SEQUENCE: 50
tgtctaacaa ttcgttcaag ccgacgc                                          27

SEQ ID NO: 51           moltype = DNA  length = 25
FEATURE                 Location/Qualifiers
source                  1..25
                        mol_type = other DNA
                        organism = synthetic construct
SEQUENCE: 51
ctcgagagat ctgatatcac tctag                                            25

SEQ ID NO: 52           moltype = DNA  length = 47
FEATURE                 Location/Qualifiers
source                  1..47
                        mol_type = other DNA
                        organism = synthetic construct
SEQUENCE: 52
gcttaattca ggagttaaac atcatgagcc atattcaacg ggaaacg                    47

SEQ ID NO: 53           moltype = DNA  length = 34
FEATURE                 Location/Qualifiers
source                  1..34
                        mol_type = other DNA
                        organism = synthetic construct
SEQUENCE: 53
ttagaaaaac tcatcgagca tcaaatgaaa ctgc                                  34

SEQ ID NO: 54           moltype = DNA  length = 50
FEATURE                 Location/Qualifiers
source                  1..50
                        mol_type = other DNA
                        organism = synthetic construct
SEQUENCE: 54
tgtctatact ccagttactc aatacgtaac aataatcagt ttatcctaac                 50

SEQ ID NO: 55           moltype = DNA  length = 32
FEATURE                 Location/Qualifiers
source                  1..32
                        mol_type = other DNA
                        organism = synthetic construct
SEQUENCE: 55
atcgaaacct ttcttaaaat cttttagacg ag                                    32

SEQ ID NO: 56           moltype = DNA  length = 23
FEATURE                 Location/Qualifiers
source                  1..23
                        mol_type = other DNA
                        organism = synthetic construct
SEQUENCE: 56
ggctctaaag aaaagacaga ggc                                              23

SEQ ID NO: 57           moltype = DNA  length = 36
FEATURE                 Location/Qualifiers
source                  1..36
                        mol_type = other DNA
                        organism = synthetic construct
SEQUENCE: 57
gaaagctctt atggtggttg ctgttccgct accgct                                36

SEQ ID NO: 58           moltype = DNA  length = 36
FEATURE                 Location/Qualifiers
source                  1..36
                        mol_type = other DNA
                        organism = synthetic construct
SEQUENCE: 58
gaacagcggt agcggaacag caaccaccat aagagc                                36

SEQ ID NO: 59           moltype = DNA  length = 45
FEATURE                 Location/Qualifiers
source                  1..45
                        mol_type = other DNA
                        organism = synthetic construct
SEQUENCE: 59
accagctcac cgtctttaac tttcatatcg gcgtacaaga agaag                      45

SEQ ID NO: 60           moltype = DNA  length = 44
FEATURE                 Location/Qualifiers
source                  1..44
```

```
                         mol_type = other DNA
                         organism = synthetic construct
SEQUENCE: 60
agcaaccacc ataagagctg caacggtaat caagcaaagc aatg                  44

SEQ ID NO: 61            moltype = DNA  length = 24
FEATURE                  Location/Qualifiers
source                   1..24
                         mol_type = other DNA
                         organism = synthetic construct
SEQUENCE: 61
gctcttatgg tggttgctgt tccg                                        24

SEQ ID NO: 62            moltype = DNA  length = 50
FEATURE                  Location/Qualifiers
source                   1..50
                         mol_type = other DNA
                         organism = synthetic construct
SEQUENCE: 62
gctcgagatc tgatatcact gtcacagtca aaaatgcaga ctaattcacc            50

SEQ ID NO: 63            moltype = DNA  length = 20
FEATURE                  Location/Qualifiers
source                   1..20
                         mol_type = other DNA
                         organism = synthetic construct
SEQUENCE: 63
gcgcccatca gcttttaaga                                             20

SEQ ID NO: 64            moltype = DNA  length = 20
FEATURE                  Location/Qualifiers
source                   1..20
                         mol_type = other DNA
                         organism = synthetic construct
SEQUENCE: 64
gcgcccatca gcttttaaga                                             20

SEQ ID NO: 65            moltype = DNA  length = 204
FEATURE                  Location/Qualifiers
source                   1..204
                         mol_type = other DNA
                         organism = synthetic construct
SEQUENCE: 65
atgcttcata aaagccgtat aaaaattaaa aacacgcttt ctgaagctaa atatatttta  60
gagcatttgt gggattctgc tctgcaatgg ccattgcttt gcttgattac cgttgccgct  120
cttatggtgg ttgctgttcc gctaccgctt tattatcaat gggtctatgg cattttttt  180
tatgggattg acgctgctga ttga                                        204

SEQ ID NO: 66            moltype = DNA  length = 600
FEATURE                  Location/Qualifiers
source                   1..600
                         mol_type = other DNA
                         organism = synthetic construct
SEQUENCE: 66
ttaactttca tatcggcgta caagaagaag aaatcccctt tttgtctgtc gaaacgatgg  60
atgaattata tcaggcttcg caggattttt cagggattac tcttgcggat ctaggaacgg  120
aaatccctaa atccagcata gcccaagaaa acattcttca tatttccatt ttgtctccca  180
atgcaggatg tatggctctg tttcccgaag cctttgacaa gcagcattac tacatcatca  240
ataatgaaaa tgaccgctat aattttcctc gtgcggcctc tcaatttgtg caggacatgg  300
ttcaagacaa tttaatcggc atcatccgtc aggatgaagc ggtgaatgaa gccttgggga  360
aattacagcc tttacatctt tatgcgccga cctctgtcgc cttaaaagat tttgataact  420
gcgcccatca gcttttaaga atgatagaaa tgaatatttc gcgtcatgcg gaggtatccg  480
ccgatgcttc ataaaagccg tataaaaatt aaaaacacgc tttctgaagc taaatatatt  540
ttagagcatt tgtgggattc tgctctgcaa tggccattgc tttgcttgat taccgttgcc  600

SEQ ID NO: 67            moltype = DNA  length = 600
FEATURE                  Location/Qualifiers
source                   1..600
                         mol_type = other DNA
                         organism = synthetic construct
SEQUENCE: 67
gctcttatgg tggttgctgt tccgctaccg ctttattatc aatgggtcta tggcattttt  60
tttatgggat tgacgctgct gattgatcgc agcccaagcc attttgcctc tattgttatc  120
tgtctttcct ctattctgac ttcaacccga tatatctttt ggcgcattac gcaaacattg  180
cgttttgacc acatcatgga cgccgttttt ggtggggttc tgtttatggc agagctttat  240
gcatgggcta ttcttatatt agggttgttc cagattttat ggccgatgca gcgtcctgtt  300
gtcccgttat caggcgagga tgaagagtta cctacagttg atgtctttat tccgacttat  360
aacgaaagca tggaaatcgt tcaaaatacc gttttcgcgg ctttgggaat ggattatcca  420
aaagaccgct ttaacgttta tctgttggat gatggtcatc gagaagaatt ccgccttttt  480
```

-continued

```
gcagaagagg cgggatgcca ttatttaacc cgtaatgata atctgaatgc caaggcgggt  540
aacctaaatg cggccttgaa aaagaccaaa ggtgaattag tctgcatttt tgactgtgac  600

SEQ ID NO: 68          moltype = DNA  length = 1434
FEATURE                Location/Qualifiers
source                 1..1434
                       mol_type = other DNA
                       organism = unidentified
SEQUENCE: 68
ctatcgaaag gcaaatttct ttctcgccga gcctgtgagc gaagcgagca gcgccgagag  60
attaacgggc ggtgggcttt gagaaggatc gctatcaggc tttcgattat aaatagcgtc  120
tacactgtct gcggcaggag cagtgcagtc cttatcttct tctttggttt ttagttttgt  180
atggtcgcta ttagataaat aagtataaca ggatagagta taagaattga actcgcgttg  240
attgtccgag atttggggct tttttgaggt atcctccttg gaggttttag aagatatttt  300
aacctcttcc tgatcagtct gtgctgcctt cttagcctga gcttcttgtt cccgttgttc  360
cgcccgctcg atagatttgg cgagctgtat gagcgaatcc gttagctctg ttggttcttt  420
attgtccgat atcgctttga cgaaatcttc gggaggcaag ctttcaacga tagccttggt  480
ttcggctttg tccgcctctt gggcgtggtc aatatcgtca ggaataggcg cattcctccg  540
gcgcatgacg cgctcgaaaa cctgtctggc caactctggc caatccttgg gagacaagaa  600
gccgtaggcg ttactggtct gcttacggcg ggggcctttg ccatccgccg tgatcttgat  660
tgatcggcgt atccagcgga tgaagcctaa atcctgtaat tgccgcagta atttgacgac  720
cgtcgcacgg gcatagccga cacgatcgca tattgtgtcg agggtcggct ctaaccgacc  780
agttttaaag tcgaccatcc gaaacagcat ctttagaagg cgaacggcct tatcgcttaa  840
gcccttggtt ttgatcgaat attgatcgac cgcttccaga taggcaccga tctcttgcgg  900
attgaccggc ttccagaccg acttctcgcg ttcgccaacc tcataagaat cccgatgcac  960
aggatcagga gtttgacggc gggttttata gcgaatggct cgttcgagag ggtctctacg  1020
tctcgcaata gctgttttgc gagcaatatc tgcagcggtt tcaggatcac atccgctaga  1080
taccatctga tcaaaatatt ctatctcgtc gaaatctgat gcggaggctg taacctcact  1140
attggtattt gaggccggaa tttcgggatg agcgctattg gccaaggaca ttgatttaga  1200
gaatgcacgg tctattttat gctgttctgc ggctcgatct gccataatct ttgcgctatc  1260
atatggcata cccgtttcaa ccaacatggc tcgataagtg ccacgcttga aacggcctag  1320
cctgtcgata aaaggactgg ttacgggcgt cgtttgttca aaagacgcag agacaggctc  1380
taaagaaaag acagaggcat ccgagagtgt cgctgaagag gaagaggcag tcat        1434
```

GENETICALLY ENGINEERED *ZYMOMONAS MOBILIS* ZM4 FOR PRODUCING PHB AND USES THEREOF

CROSS-REFERENCE TO RELATED APPLICATIONS

This application claims priority to Chinese Patent Application NO. 202111642567.5, filed with China National Intellectual Property Administration on Dec. 29, 2021, and Chinese Patent Application NO. 202111646334.2, filed with China National Intellectual Property Administration on Dec. 29, 2021; the entire contents of which are incorporated herein by reference.

SEQUENCE LISTING

The sequence listing xml file submitted herewith, named "WIUS224921P_SeqList.xml", created on Aug. 13, 2023, and having a file size of 80,542 bytes, is incorporated by reference herein.

TECHNICAL FIELD

This disclosure relates to genetically engineered strains of *Zymomonas mobilis*. Specifically, this disclosure relates to a genetically engineered *Zymomonas mobilis* ZM4 for producing PHB and uses thereof.

BACKGROUND

The statements herein provide background information relevant to the present disclosure only and do not necessarily constitute prior art.

Plastics produced in petroleum industry possess good flexibility and lightness. It has become an indispensable commodity in people's life. However, petroleum-derived plastics have low biodegradability, complicated recycling and classification, and serious environmental pollution, especially to marine ecosystems. Poly-p-hydroxybutyric acid (PHB) is a kind of high polymer polyester synthesized by microorganisms, which has biodegradability and biocompatibility. Therefore, PHB is considered as an environmentally friendly material, and is widely used in agriculture, environmental protection, biochemistry, medicine, medical materials and many other fields.

The biosynthesis of PHB mainly adopts microbial self-metabolism, wherein the most utilized method is microbial fermentation, which is also widely studied. But at present, most microbial fermentation processes are aerobic, requiring a large amount of energy to supply oxygen. As a facultative anaerobic Gram-negative bacteria, *Zymomonas mobilis* (abbreviated *Z. mobilis*) has many unique physiological characteristics and excellent industrial production characteristics. It is the only one known microorganism that is capable of utilizing 2-keto-3-deoxy-6-phosphogluconic acid (Entner-Doudoroff, ED) pathway under anaerobic conditions, and has excellent properties such as high sugar absorption rate, high ethanol yield and high ethanol tolerance. At present, lactic acid, 2-3 butanediol, isobutanol and many other products have been manufactured by *Z. mobilis*. As a facultative anaerobic organism, *Z. mobilis* can ferment under anaerobic conditions and perform better than aerobic conditions, thus oxygen supply problems such as stirring, ventilation and air sterilization, faced by the microbial aerobic fermentation process can be solved. In addition, a previous study in 2006 found that the heterologous expression of the PHB synthesis genes in *Z. mobilis* could accumulate 0.7% (dry cell weight, dcw) PHB and promote ethanol production to a certain extent.

SUMMARY

Embodiments provide a genetically engineered strain ZM4Pt of *Z. mobilis* ZM4 and uses thereof. ZM4Pt is a genetically engineered strain that is obtained by transferring a recombinant plasmid into *Z. mobilis* ZM4. The recombinant plasmid carrys an operon composed of three essential genes (phaA, phaB, phaC) for PHB synthesis and tetracycline inducible promoter (Ptet) with their codons optimized.

Embodiments provide a genetically engineered strain ZM4Pg of *Z. mobilis* ZM4 and uses thereof. ZM4Pg is a genetically engineered strain obtained by replacing the promoter on the Ptet-phaCAB operon with a strong promoter Pgap.

Embodiments provide a genetically engineered strain ZMPt of *Z. mobilis* ZM4 and uses thereof. ZMPt is a genetically engineered strain obtained by integrating an operon Ptet-phaCAB into the ZMO0038 position of the ZM4 genome by using a endogenous CRISPR-Cas system of *Z. mobilis* ZM4.

Embodiments provide a genetically engineered strain $ZMPt^g$ of *Z. mobilis* ZM4 and uses thereof. $ZMPt^g$ is a genetically engineered strain obtained by transferring a recombinant plasmid pEZ-Pg into ZMPt. The recombinant plasmid pEZ-Pg carrys an operon Pgap-phaCAB with a strong promoter Pgap. Thus, $ZMPt^g$ contains two copies of phaCAB, one copy located in ZMO0038 of its genome and another located in the plasmid pEZ-Pg.

Embodiments provide a genetically engineered strain ZMPg of *Z. mobilis* ZM4 and uses thereof. ZMPg is a genetically engineered strain obtained by integrating a Pgap-phaCAB operon into the ZMO0038 gene position on the ZM4 genome by using its endogenous CRISPR-Cas system.

Embodiments provide a genetically engineered strain $ZMPg^g$ of *Z. mobilis* ZM4 and uses thereof. $ZMPg^g$ is a genetically engineered strain obtained by transferring a recombinant plasmid pEZ-Pg into ZMPg. The recombinant plasmid pEZ-Pg carrys an operon Pgap-phaCAB with a strong promoter Pgap. Thus, $ZMPg^g$ contains two copies of phaCAB, one copy located in ZMO0038 of its genome and another located in the plasmid pEZ-Pg.

Embodiments provide two genetically engineered strains $ZMPt^{N1}$ and $ZMPt^{N2}$ of *Z. mobilis* ZM4 and uses thereof. $ZMPt^{N1}$ is a genetically engineered strain that is obtained by transferring a recombinant plasmid into ZMPt, the recombinant plasmid carrys an operon Pgap-ppnK-phaCAB. ZMPtN2 is a genetically engineered strain that is obtained by transferring a recombinant plasmid into ZMPt, the recombinant plasmid carrys an operon Pgap-zwf-phaCAB.

Embodiments provide two genetically engineered strains $ZMPt^{N1\text{-}EUP}$ and $ZMPt^{N2\text{-}EUP}$ of *Z. mobilis* ZM4 and uses thereof. $ZMPt^{N1\text{-}EUP}$ is a genetically engineered strain that is obtained by transferring a recombinant plasmid into $ZMPt^{N1}$. $ZMPt^{N2\text{-}EUP}$ is a genetically engineered strain that is obtained by transforming a recombinant plasmid into $ZMPt^{N2}$. The recombinant plasmid carrying ada gene from *Dickeya zeae* (abbreviated *D. zeae*) and adh2 gene from *Saccharomyces cerevisiae* (abbreviated *S. cerevisiae*) is used to construct a heterologous ethanol utilization pathway (EUP).

Embodiments provide a genetically engineered strain ZMPt-Flo of *Z. mobilis* ZM4 and uses thereof. ZMPt-flo is a flocculation genetically engineered strain obtained by knocking out specific nucleotide thymidine (T) in the ZMO1082 gene of genetically engineered strain ZMPt.

Embodiments provide a genetically engineered strain ZMPt-Flo$^{N2}$ of *Z. mobilis* ZM4 and uses thereof. ZMPt-FloN$^{2}$ is a flocculation genetically engineered strain obtained by transferring a recombinant plasmid into ZMPt-Flo. The recombinant plasmid carrys the Pgap-zwf-phaCAB operon.

Embodiments provide a genetically engineered strain ZMPt-Flo$^{N2-EUP}$ of *Z. mobilis* ZM4 and uses thereof. ZMPt-Flo$^{N2-EUP}$ is a flocculation genetically engineered strain obtained by transferring a recombinant plasmid into ZMPt-Flo$^{N2}$. The recombinant plasmid carrying ada gene from *D. zeae* and adh2 gene from *S. cerevisiae* is used to construct a heterologous ethanol utilization pathway (EUP).

DETAILED DESCRIPTION OF THE EMBODIMENTS

Embodiments of this disclosure provide genetically engineered strains of *Z. mobilis* ZM4 for PHB and ethanol production and its application. Embodiments used *Z. mobilis* ZM4 as the starting strain, modified ZM4 by means of genetic engineering, introduced specific exogenous genes for PHB and ethanol production in *Z. mobilis* ZM4, that had improved the yield of PHB through a series of genetic engineering and metabolic engineering modifications, and finally achieved the co-production of ethanol and PHB.

Figure 1:
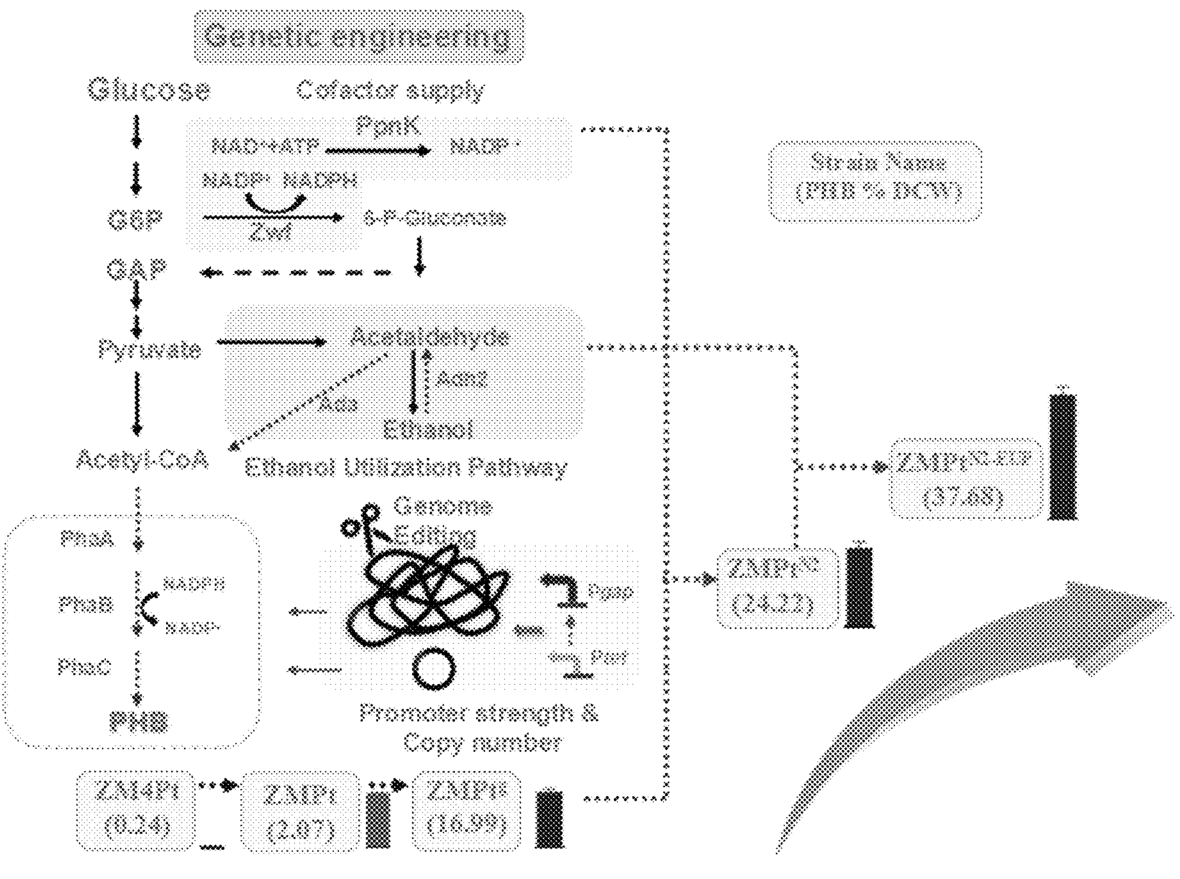
FIG. 1 illustrates a flow chart of genetic engineering strategies for *Z. mobilis* ZM4 genetically engineered strains, in accordance with embodiments.
Figure 2:
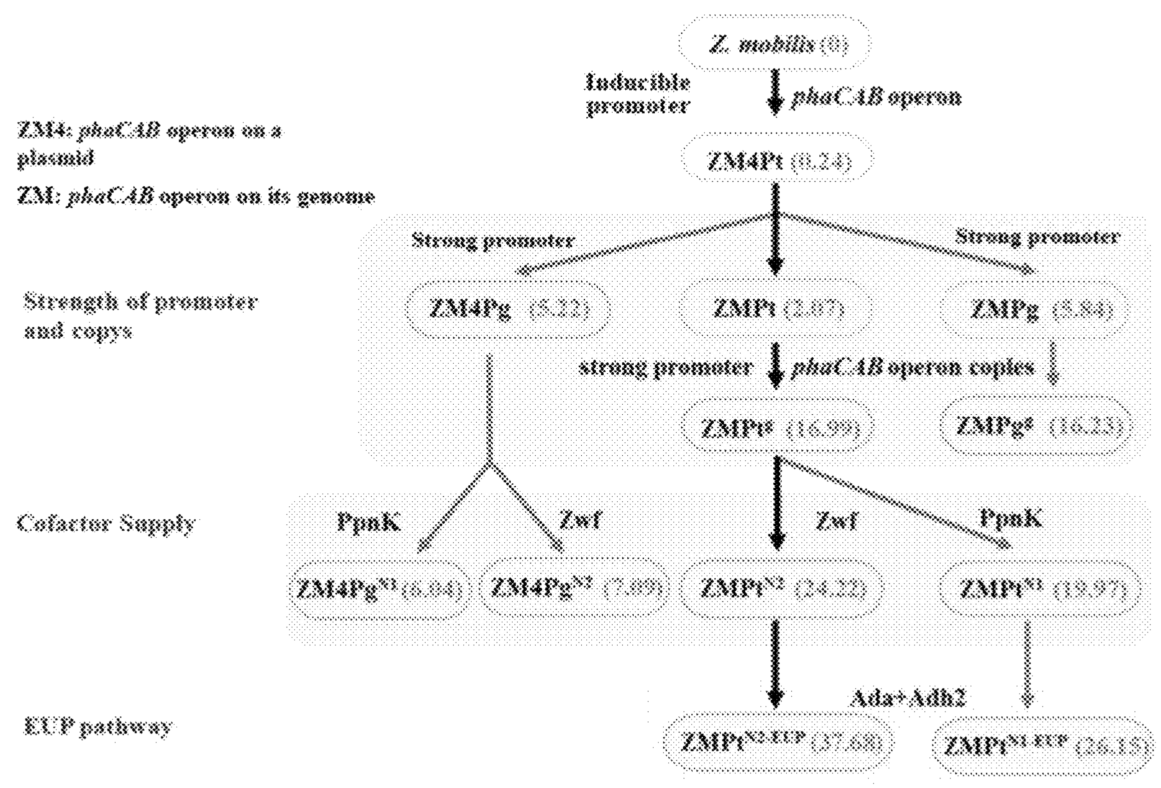
FIG. 2 illustrates a flow chart for construction of a genetically engineered strain of *Z. mobilis* ZM4 for PHB and ethanol production in accordance with embodiments.
Figure 13:
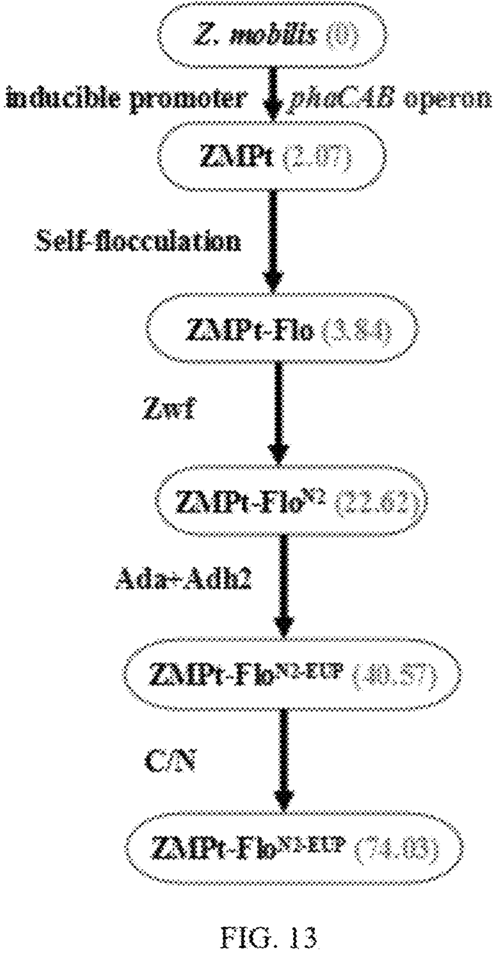
FIG. 13 illustrates a flow chart for construction of a genetically engineered strain of *Z. mobilis* ZM4 for PHB and ethanol production in accordance.
Figure 16:
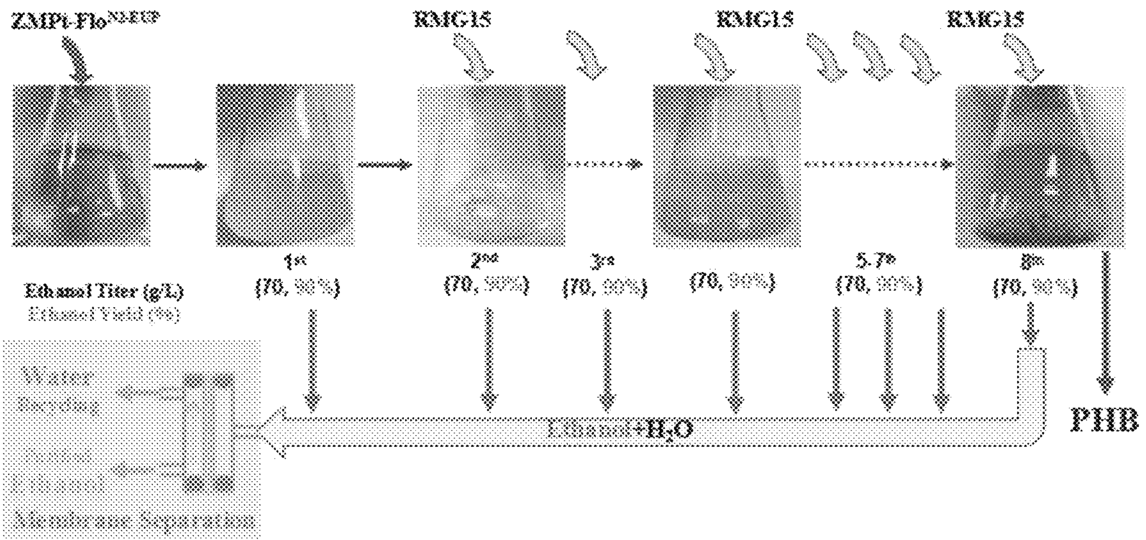
FIG. 16 illustrates a flow chart of continuous cycle fermentation of ZMPt-Flo$^{N2-EUP}$.

The acquisition process of a few genetically engineered strains including genetic engineering for co-production of ethanol and PHB of *Z. mobilis* ZM4 are shown in FIG. 1 and FIG. 16, and strain construction process of co-production of ethanol and PHB of *Z. mobilis* ZM4 are shown in FIG. 2 and FIG. 13.

Among embodiments, by taking *Z. mobilis* ZM4 as the starting strain, a recombinant vector was transferred into *Z. mobilis* ZM4 by means of genetic engineering, thus a few genetically engineered strains capable of producing ethanol and PHB together had been obtained. The recombinant vector carrying an operon (Ptet-phaCAB) was composed of three essential genes phaA, phaB, phaC and tetracycline inducible promoter (Ptet). Furthermore, various approaches were applied to help boost the yield of PHB production for these genetically engineered strains, which include enhancing the promoter strength, increasing the copy number of PHB synthesis gene, introducing genes for a balanced cofactor supply, introducing exogenous ethanol utilization pathway, and optimizing fermentation conditions.

As shown in FIG. 2, embodiments provided a genetically engineered strain ZM4Pt of *Z. mobilis* ZM4 and uses thereof. ZM4Pt was obtained by transferring a recombinant plasmid into *Z. mobilis* ZM4. The recombinant plasmid carrying an operon was composed of three codon-optimized essential genes (phaA, phaB, phaC) for PHB synthesis and the tetracycline inducible promoter (Ptet).

As shown in FIG. 2, embodiments provided a genetically engineered strain ZM4Pg of *Z. mobilis* ZM4 and uses thereof. ZM4Pg was obtained by replacing the Ptet promoter on the Ptet-phaCAB operon of ZM4Pt with a strong promoter Pgap.

As shown in FIG. 2, embodiments provided a genetically engineered strain ZMPt of *Z. mobilis* ZM4 and uses thereof. ZMPt was obtained by integrating an operon Ptet-phaCAB into the ZMO0038 position of the ZM4Pt genome using the endogenous CRISPR-Cas system of *Z. mobilis* ZM4.

As shown in FIG. 2, embodiments provided a genetically engineered strain ZMPt$^{g}$ of *Z. mobilis* ZM4 and uses thereof. ZMPt$^{g}$ was obtained by transferring a recombinant plasmid pEZ-Pg into ZMPt. The recombinant plasmid pEZ-Pg possessed an operon Pgap-phaCAB with a strong promoter Pgap. Thus, ZMPt$^{g}$ contained two copies of phaCAB, one copy located in ZMO0038 of its genome and another located in plasmid pEZ-Pg.

As shown in FIG. 2, embodiments provided a genetically engineered strain ZMPg of *Z. mobilis* ZM4 and uses thereof. ZMPg was obtained by integrating a operon Ptet-phaCAB operon into the ZMO0038 gene position on the ZM4 genome and using its endogenous CRISPR-Cas system.

As shown in FIG. 2, embodiments provided a genetically engineered strain ZMPg$^{g}$ of *Z. mobilis* ZM4 and uses thereof. ZMPg$^{g}$ was obtained by transferring a recombinant plasmid pEZ-Pg into ZMPg. The recombinant plasmid pEZ-Pg possessed an operon Pgap-phaCAB with a strong promoter Pgap. Thus, ZMPg$^{g}$ contained two copies of phaCAB, one copy located in ZMO0038 of its genome and another located in plasmid pEZ-Pg.

As shown in FIG. 2, embodiments provided two genetically engineered strains ZMPt$^{N1}$ and ZMPt$^{N2}$ of *Z. mobilis* ZM4 and uses thereof. ZMPt$^{N1}$ was obtained by transferring a recombinant plasmid into ZMPt, and the recombinant plasmid possessed an operon Pgap-ppnK-phaCAB. ZMPt$^{N2}$ was obtained by transferring a recombinant plasmid into ZMPt, and the recombinant plasmid possessed an operon Pgap-zwf-phaCAB.

As shown in FIG. 2, embodiments provided two genetically engineered strains ZMPt$^{N1-EUP}$ and ZMPt$^{N2-EUP}$ of *Z. mobilis* ZM4 and uses thereof. ZMPt$^{N1-EUP}$ was obtained by transferring a recombinant plasmid into ZMPt$^{N1}$. ZMPt$^{N2-EUP}$ was obtained by transforming a recombinant plasmid into ZMPt$^{N2}$. The recombinant plasmid possessing ada gene from *D. zeae* and adh2 gene from *S. cerevisiae* was used to construct a heterologous ethanol utilization pathway (EUP).

As shown in FIG. 13, embodiments provided a genetically engineered self-flocculation strain ZMPt-Flo of *Z. mobilis* ZM4 and uses thereof. ZMPt-Flo was obtained by knocking out specific nucleotide thymidine (T) in the ZMO1082 gene of genetically engineered strain ZMPt.

As shown in FIG. 13, embodiments provided a genetically engineered self-flocculation strain ZMPt-Flo$^{N2}$ of *Z. mobilis* ZM4 and uses thereof. ZMPt-Flo$^{N2}$ was a genetically engineered strain obtained by transferring a recombinant plasmid into ZMPt-Flo. The recombinant plasmid possessed the Pgap-zwf-phaCAB operon.

As shown in FIG. 13, embodiments provided a genetically engineered self-flocculation strain ZMPt-Flo$^{N2-EUP}$ of *Z. mobilis* ZM4 and uses thereof. ZMPt-Flo$^{N2-EUP}$ was obtained by transferring a recombinant plasmid into ZMPt-Flo$^{N2}$. The recombinant plasmid possessing ada gene from *D. zeae* and adh2 gene from *S. cerevisiae* was used to construct a heterologous ethanol utilization pathway (EUP).

Embodiments also disclosed a method of the application of genetically engineered bacteria in the simultaneous production of ethanol and PHB, wherein the genetically engineered bacteria was selected from the group consisting of a strain named ZMPt$^{N1-EUP}$ a strain named ZMPt$^{N2-EUP}$ strain, or a strain named ZMPt-Flo$^{N2-EUP}$.

In some embodiments, the applications in simultaneous production of ethanol and PHB by the ZMPt$^{N1-EUP}$ strain included: inoculating the ZMPt$^{N1}$-EUP strain into a 100 mL triangular flask with 80% RMG5 medium for bottling volume, wherein the tetracycline inducer concentration was 1.2 μg/mL with a initial $OD_{600nm}$ of 0.1; and incubating at 30° C. with a 100 rpm shaker.

In some embodiments, the applications in the simultaneous production of ethanol and PHB by the ZMPt$^{N2}$-EUP strain included: inoculating the ZMPt$^{N2}$-EUP strain into a 100 mL triangular flask with 80% RMG5 medium for bottling volume, wherein the tetracycline inducer concentration was 1.2 μg/mL with a initial $OD_{600nm}$ of 0.1; and incubating at 30° C. with a 100 rpm shaker.

In some embodiments, the applications in the simultaneous production of ethanol and PHB by the ZMPt-Flo$^{N2-EUP}$ strain included: inoculating the ZMPt-Flo$^{N2-EUP}$ strain into a 100 mL triangular flask with 80% RMG5 medium for bottling volume, wherein the tetracycline inducer concentration was 1.2 μg/mL with a initial $OD_{600nm}$ of 0.1; and incubating at 30° C. with a 100 rpm shaker.

In some embodiments, the medium used for fermentation production was RMG5 medium with a C/N ratio of 5~10:1.

In some embodiments, the ZMPt-Flo$^{N2}$-EUP strain was used for producing ethanol and PHB simultaneously.

In the embodiments, the ZMPt$^{N1-EUP}$ strain was a genetically engineered strain obtained by transferring a recombinant plasmid pE39p-PeEUP into ZMPt$^{N1}$ strain. And the ZMPtN1 strain was obtained by transferring a recombinant plasmid pEZ-Pg$^{N1}$ into ZMPt strain.

In the embodiments, the ZMPt$^{N2-EUP}$ strain was a genetically engineered strain obtained by transferring the recombinant plasmid pE39p-PeEUP into ZMPt$^{N2}$ strain, which was obtained by transferring a recombinant plasmid pEZ-Pg$^{N2}$ into the ZMPt strain.

In some embodiments, the ZMPt-Flo$^{N2-EUP}$ strain was a genetically engineered strain obtained by transferring the recombinant plasmid pE39p-PeEUP into the ZMPt-Flo$^{N2}$ strain, which was obtained by transferring the recombinant plasmid pEZ-Pg$^{N2}$ into the ZMPt-Flo strain.

In some embodiments, the ZMPt$^{9}$ strain was a genetically engineered strain obtained by transferring the recombinant plasmid pEZ-Pg into the ZMPt strain, which was obtained by replacing the ZMO0038 gene of ZM4 strain genome with the Ptet-phaCAB operon. The ZMPt-Flo strain was obtained by replacing the genome ZMO0038 of ZM4 strain with the Ptet-phaCAB operon and knocking out the nucleotide thymidine at the 181$^{th}$ position of ZMO082 gene.

In some embodiments, the pEZ-Pt plasmid was recombined by ligation of the Ptet-phaCAB operon to the pEZ15A vector.

In some embodiments, the pEZ-Pg plasmid was constructed by replacing the inducible promoter Ptet of the pEZ-Pt plasmid with the strong promoter Pgap.

In some embodiments, the pEZ-Pg$^{N1}$ plasmid was constructed by ligating gene ZMO1329 to the pEZ-Pg plasmid.

In some embodiments, the pEZ-Pg$^{N2}$ plasmid was constructed by ligating gene ZM00367 to the pEZ-Pg plasmid.

In some embodiments, the pE39p-PeEUP plasmid was constructed by constructing ada and adh2 genes linked by RBS sequence into the shuttle vector pEZ39p plasmid. The pEZ39p plasmid was constructed by replacing the replicon of the pEZ15A plasmid with the replicon of 39-032 in the endogenous plasmid from ZM4. Therein, the Ptet-phaCAB operon had a nucleotide sequence formed by a sequential connection of Ptet, phaC, RBS, phaA, RBS and phaB elements. The nucleotide sequences of phaC, phaA and phaB are shown in sequence as SEQ ID NO: 1~3. Described RBS sequence is shown as SEQ ID NO: 4. ada and adh2 gene sequences are respectively shown as SEQ ID NO: 39 and SEQ ID NO: 40. The replicon sequence of the 39-032 endogenous plasmid is shown as SEQ ID NO: 41.

In some embodiments, the construction method of the pEZ39p plasmid included: obtaining the 39-032 replicon fragment and the vector fragment on the pEZ15A plasmid, and ligating the 39-032 replicon fragment with the vector fragment on the pEZ15A plasmid by Gibson assembly. Therein, the 39-032 replicon fragment was obtained by PCR amplification using 39-032-p-spe-F (SEQ ID NO: 42) and 39-032-p-spe-R (SEQ ID NO: 43) as primers and ZM4 strain as DNA amplification template. The vector fragment on the pEZ15A plasmid was obtained by PCR amplification using pEZ15A as DNA amplification template and using pEZ-dp-anti-F (SEQ ID NO: 44) and pEZ-dp-anti-R (SEQ ID NO: 45) as primers.

In some embodiments, the construction of the pEZ-Pg$^{N2}$ plasmid included the following steps (1) to (4):

(1) phaCAB fragment on Ptet-phaCAB operon was amplified with primers Zwf-phaC-F and phaB-R. Therein, the nucleotide sequence of primer Zwf-phaC-F is aaagaggagaaaggatctcccatggccaccggcaaagg, shown as SEQ ID NO:38; the nucleotide sequence of primer phaB-R is ggccgctactagtttaacccatatgcaagccaccattc, shown as SEQ ID NO: 13;

(2) zwf fragment of ZM00367 gene was connected with phaCAB fragment to obtain zwf-phaCAB fragment;

(3) The zwf-phaCAB fragment was linked to the Pgap promoter to form the Pgap-zwf-phaCAB operon;

(4) pEZ-Pg$^{N2}$ was obtained by assembling Pgap-zwf-phaCAB operon with pEZ-15A reverse expansion vector fragment.

In some embodiments, the construction method of the pEZ-Pg plasmid included the following steps (1) to (3):

Pgap-CAB-F and phaB-R were used as primers, and pEZ-Pt plasmid was used as DNA template for amplification to obtain the phaCAB fragment with homologous arms between Pgap promoter and phaCAB. Therein, the nucleotide sequence of primer Pgap-CAB-F is cttaataagttaggagaataaacatggccaccggcaaag, shown as SEQ ID NO:18;

Pgap-phaCAB fragment was obtained by an Overlap PCR linking the phaCAB fragment with the Pgap promoter;

The Pgap-phaCAB fragment and pEZ15A vector skeleton containing the screening resistance gene of spectinomycin were assembled at a molar ratio of 3:1 to obtain the plasmid pEZ-Pg.

The technical solution of this disclosure will be clearly and completely described below in the context of embodiments.

Construction and Application of Genetically Engineered Strain ZM4Pt

In this embodiment, the phaCAB operon was obtained by concatenating the genes of PHB synthetase (PhaC), 3-keto thiolase (PhaA) and acetyl-acetyl-CoA reductase (PhaB) from *Ralstonia eutropha* H16. The phaCAB operon was integrated into the plasmid pEZ15A, and then the tetracycline inducible promoter Ptet was used to control the gene expression level to obtain the recombinant plasmid pEZ-Pt. The recombinant plasmid pEZ-Pt was transferred into *Z. mobilis* ZM4 (ATCC31821) to obtain the genetically engineered strain ZM4Pt that is capable of PHB synthesis. After fermentation, the PHB and ethanol production induced by different tetracycline were detected in fermentation broth of ZM4Pt.

1. Preparation of the Fragment of Ptet-phaCAB Operon

Figure 3:
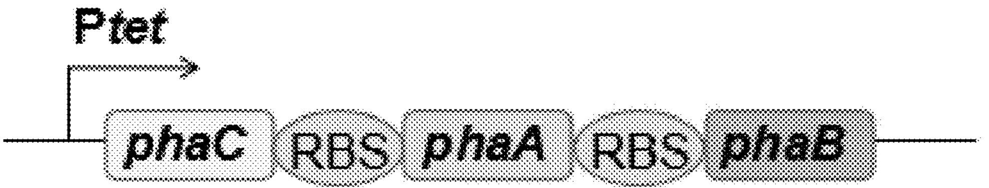
FIG. 3 illustrates the structure of a recombinant plasmid pEZ-Pt, in accordance with embodiments.

As shown in FIG. 3, according to the connection sequence of Ptet-phaC-RBS-phaA-RBS-phaB, phaC (SEQ ID NO:1), phaA (SEQ ID NO:2) and phaB (SEQ ID NO:3) were sequentially linked to obtain the Ptet-phaCAB operon. In the sequence of Ptet-phaCAB, from 5'end to 3' end, position 1 to 624 is Ptet sequence (SEQ ID NO:5), position 2395 to 2418 and position 3601 to 3624 are RBS sequence (SEQ ID NO:4).

The construction process of Ptet-phaCAB operon (SEQ ID NO:7) included the following steps:

The DNA molecules of Ptet, phaC, phaA and phaB were synthesized and codon-optimized by Censcript (Nanjing, China), which were respectively used as DNA amplification templates, and the target fragments were amplified with primers (the underlined part is the homologous arm). Therein, the primers used to amplify these DNA molecules are as follows:

The nucleotide sequence of Ptet-CAB-F primer is: gatctcccggatccatggccaccggcaaag, SEQ ID NO:8.

The nucleotide sequence of phaC-R primer is:

SEQ ID NO: 9
cttactttctctagattatggttaggctttagctttaacataacgacc
ag.

The nucleotide sequence of phaA-F primer is

SEQ ID NO: 10
ccataatctagagaaagtaagcacatgaccgatgttgtcattgtctct
g.

The nucleotide sequence of phaA-R primer is:

SEQ ID NO: 11
gtgcttactttctctagattatggttatttgcgttcaacggccaaag.

The nucleotide sequence of phaB-F primer is: ctagagaaagtaagcacatgacccaacgtattgcctatc, SEQ ID NO:12.

The nucleotide sequence of phaB-R primer is: ggccgctactagtttaacccatatgcaagccaccattc, SEQ ID NO:13.

The nucleotide sequence of Ptet-F primer is: cggccgcttctagagttaagacccactttcacatttaagttg, SEQ ID NO:14.

The nucleotide sequence of Ptet-R primer is: gggagatcctttctcctctttagatc, SEQ ID NO:15.

After amplification with the above primers, the 3' end of the target fragment Ptet has a homologous sequence with the 5' end of the target fragment phaC. The 3' end of the target fragment phaC has a homologous sequence with the 5' end of the target fragment phaA. The 3' end of phaA has a homologous sequences with the 5' end of phaB. The 3' end of phaB has a homology sequence with pEZ15A vector. Therefore, according to the principle of pairwise linkage of homologous sequences, an Overlap PCR reaction was used to connect the target fragments Ptet, phaC, RBS1, phaA, RBS2 and phaB together successively, namely, the Ptet-phaCAB operon fragment was obtained. Therein, the two ends of RBS1 contain homologous sequences to phaC and phaA, respectively. The two ends of RBS2 contain homologous sequences to phaA and phaB, respectively. Specifically, the Overlap PCR reaction process included:

Step1: The reagents were mixed to form the reaction system as shown in Table 1, and PCR reaction was performed. The PCR reaction conditions were set as follows: pre-denaturation at 98° C. for 3 min; 26 cycles of denaturation at 98° C. for 10 s, annealing at 55° C. for 10 s, and extension at 72° C. for 40 s.

TABLE 1

Overlap PCR Reaction System of phaCAB

| Reagent | Volume |
|---|---|
| phaC | 1 μL |
| phaA | 1 μL |
| phaB | 1 μL |
| 2 × T5 Super PCR Mix (Tsingke) | 12.5 μL |
| 2 × T5 Primerstar (Tsingke) | 12.5 μL |
| $ddH_2O$ | To 47 μL |
| Total volume | 47 μL |

Step 2: The mixture completed in Step1 was taken out, and the primer pair composed of 1.5 μL Ptet-CAB-F and 1.5 μL phaB-R were added for PCR amplification. The PCR conditions were set as follows: pre-denaturation at 98° C. for 3 min; 26 cycles of denaturation at 98° C. for 10 s, annealing at 55° C. for 10 s, and extension at 72° C. for 40 s.

Step 3: The PCR amplification products obtained in Step2 were verified by agarose gel electrophoresis, and the target fragment phaCAB was recovered after verifing. The target fragment phaCAB and the target fragment Ptet were linked obtain by a Overlap PCR reaction, that included Step 4 and the Step 5.

Step 4: The reagents were mixed to form the PCR reaction system shown in Table 2. The PCR conditions were as follows: pre-denaturation at 98° C. for 3 min; 10 cycles of denaturation at 98° C. for 10 s, annealing at 47° C. for 10 s, and extension at 72° C. for 45 s.

Step 5: Primer pairs composed of 1.5 μL Ptet-F and 1.5 μL phaB-R were added in the mixture in step 4 for PCR amplification. The PCR conditions were set as follows: pre-denaturation at 98° C. for 3 min; 26 cycles of denaturation at 98° C. for 10 s, annealing at 55° C. for 10 s, and extension at 72° C. for 45 s. After the completion of PCR, verification was performed, and DNA was recovered to obtain the target fragment Ptet-phaCAB operon.

TABLE 2

PCR reaction system of phaCAB and Ptet ligation

| Reagent | Volume |
|---|---|
| phaCAB | 2 μL |
| Ptet | 2 μL |
| 2 × T5 Super PCR Mix (Tsingke) | 12.5 μL |
| 2 × T5 Primerstar (Tsingke) | 12.5 μL |
| $ddH_2O$ | To 47 μL |
| Total volume | 47 μL |

2. Construction of Recombinant Plasmid pEZ-Pt

In this step, the recombinant plasmid pEZ-Pt was obtained by a ligation of operon Ptet-phaCAB and the skeleton of pEZ15A vector.

Specifically, the operon Ptet-phaCAB and pEZ15A were mixed at a molar ratio of 3:1 and reacted according to the reaction system as shown in Table 3.

TABLE 3

Gibson Assembly reaction system of Ptet-phaCAB and pEZ15A

| Reagent | Volume |
|---|---|
| Ptet-phaCAB | 0.12 pM |
| pEZ15A | 0.04 pM |
| 10 × Buffer 4 (Thermo) | 0.5 μL |
| T5 Exonuclease | 0.5 U |
| $ddH_2O$ | To 5 μL |

The Gibson assembly reaction product was placed on ice for 5 min and then transferred into *E. coli* DH5a competent cells. The positive transformer pEZ-Pt was verified by colony PCR using plates containing 100 μg/mL spectinomycin.

The colony PCR detection reaction was carried out that the DNA template was ZM4, and primer pairs were composed of pEZ15A-F and pEZ15A-R, and the reaction system was shown in Table 4. The PCR reaction program was set as follows: pre-denaturation at 98° C. for 3 min; 30 cycles of denaturation at 98° C. for 10 s, annealing at 55° C. for 10 s, and extension at 72° C. (10 s/kb according to the fragment length), and the reaction is kept at 72° C. for 5 min after the end of the cycle. The PCR reaction products were collected and subjected to agarose gel electrophoresis, and the target bands consistent with expectation were validated by sequencing. PCR validation primers were as follows:

The nucleotide sequence of pEZ15A-F primer is: ggcaaagccaccctatttttag, SEQ ID NO:16.

The nucleotide sequence of pEZ15A-R primer is: cacttcactgacaccctcat, SEQ ID NO:17.

TABLE 4

Colony PCR Reaction System

| Reagent | Volume |
|---|---|
| primer(10 μM): pEZ15A-F | 0.3 μL |
| primer(10 μM): pEZ15A-R | 0.3 μL |
| 2 × T5 Super PCR Mix (Tsingke) | 5 μL |
| Template | 1 μL |
| $ddH_2O$ | To 10 μL |
| Total volume | 10 μL |

In this step, PCR was used to verify positive clones on plates by extracting plasmids from plate colonies after overnight culture using a Reagent box for plasmid extraction following standard procedures. In order to improve the efficiency of plasmid electrotransformation, the plasmid of the obtained target strain of *E. coli* DH5a was extracted and transformed into the demethylated competent cells of *E. coli* trans110, and the positive colonies on the plate were verified by colony PCR. After overnight culture, the plasmid named pEZ-Pt was extracted.

3. Preparation of Genetically Engineered Bacteria ZM4Pt

1) Preparation of ZM4 Competent Cells

An appropriate amount of ZM4 glycerol was selected by inoculation ring and spreaded on RMG5 solid medium (RMG5: 50 g/L glucose, 10 g/L yeast extract, 2 g/L $KH_2PO_4$, 3 g/L agar). The activated single colonies were obtained by inverted culturing at 30° C. for 2~3 days.

The activated single colonies were selected, transferred to 10 mL RMG5 liquid medium containing about 50 g/L glucose, 10 g/L yeast extract and 2 g/L $KH_2PO_4$, and incubated at 30° C. to the mid-logarithmic stage, and the seed solution was obtained.

The seed solution was transferred to a 250 mL flask containing 200 mL RMG5 liquid medium. The initial $OD_{600nm}$ value was controlled between 0.025 and 0.03, and the seed solution was incubated at 30° C. until the $OD_{600nm}$ value between 0.4 and 0.6.

After the bacterial solution was cooled on ice for 30 min, the bacteria were collected by centrifugation with a pre-cooled 50 mL centrifuge tube at 4000 rpm for 10 min, and the supernatant was discarded.

Add 30 mL of precooled sterile water to the centrifuge tube for resuspending and washing, centrifuge at 4000 rpm for 10 min and discard the supernatant.

Add 30 mL of pre-cooled 10% glycerol to the centrifuge tube for resuspension and washing, centrifuge at 4000 rpm for 10 min and discard the supernatant, and repeat this step again.

The bacteria was resuspended by adding 1% (volume ratio) of precooled 10% glycerol, mixed slowly and evenly, and then separated on ice. Each 50 μL was divided into sterile 1.5 mL centrifuge tubes, flash-frozen in liquid nitrogen and stored at −80° C.

2) Preparation of Genetically Engineered Bacteria ZM4Pt

ZM4 competent cells were placed on ice. After melting, 50 μL of ZM4 competent cells and 1 μg of recombinant plasmid pEZ-Pt were added for electrotransformation. The electrotransformation conditions were set at 1600 V, 25 μF, and 200Ω. After electrotransformation, the cells were resuscitated in RMG5 liquid medium in an incubator at 30° C. Cultures resuscitated for 4-6 hours were centrifuged at 6000 rpm for 1 min to remove part of the supernatant. 100 μL of suspended bacteria were spreaded on plates containing 100 μg/mL spectinomycin and incubated at 30° C. for 2 days.

After the colonies grow out, colony PCR detection was performed (the detection method is described above, and the detection reaction system is shown in Table 4).

After activating the verified correct positive transformants in the liquid RMG5 medium, the recombinant strain named ZM4Pt was preserved in 30% glycerol.

4. Fermentation Test for Genetically Engineered Bacteria ZM4Pt

The genetically engineered strain ZM4Pt was fermented in RMG5 liquid medium. 100 μL of the genetically engineered bacteria ZM4Pt was inoculated into the frozen tube containing 1 mL RMG5 (with 1 μL of spectinomycin) for cultivation. When the bacteria grown to turbidity, it was fermented in the incubator to the logarithmic stage at 30° C. Then, the samples were inoculated into RMG5 with 80% bottling volume in 100 mL triangular flask, and the fermentation was induced with different tetracycline concentrations (0, 0.2, 0.8, 1.2 μg/mL). At the beginning of fermentation, the initial value of control $OD_{600nm}$ is 0.1. In the fermentation process, UV spectrophotometer was used to measure the optical density ($OD_{600}$ nm) of the cell growth. The fermentation broth was collected at different time points for glucose and ethanol quantification using high performance liquid chromatography (HPLC).

In a HPLC detection example, 1 mL culture was centrifuged (12,000 rpm, 1 min) to obtain the supernatant for measuring the glucose and ethanol concentrations using a Shimadzu LC-2030 HPLC (LC-20AD, Shimadzu, Kyoto, Japan) equipped with refractive index detector (RID, RID-10A) and Bio-Rad Aminex HPX-87H (300×7.8 mm) column 37. Briefly, the supernatant was filtered through a 0.45-μm filter before applying on HPLC. Five millimolar (5 mM) $H_2SO_4$ was used as the mobile phase at a flow rate of 0.5 mL/min, and temperatures of the detector and column were 40 and 60° C., respectively.

5. Treatment for Fermentation Broth Samples and Determination for PHB Content

PHB detection was converted by determining the content of crotonic acid with the treatment of sulfuric acid. Then, crotonic acid can be detected by HPLC to obtain the yield of PHB correspondingly.

1) Treatment of Fermentation Broth Samples

Figure 4:
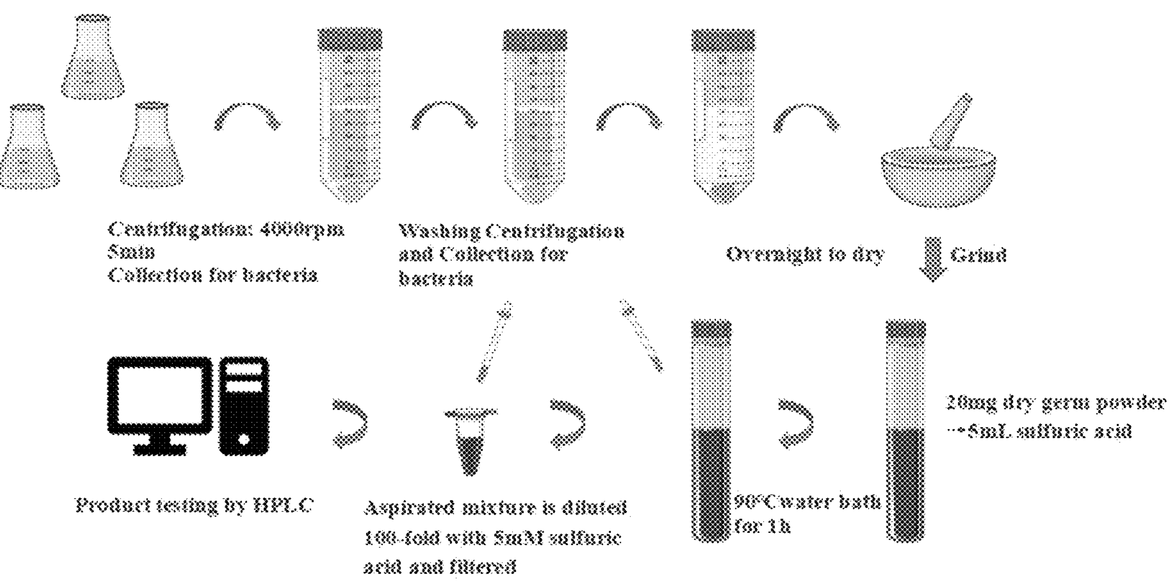
FIG. 4 illustrates a flow chart of sample handling methods with embodiments.

As shown in FIG. 4, the processes for PHB detection was provided. Specifically, the cultures at the end of fermentation were centrifuged at 4000 rpm for 8~10 min. After removing the supernatant, cell pellets were washed twice with pure water, and then centrifuged at 4000 rpm at 25° C. for 8~10 min. The final bacterial pellet was placed in an oven at 65° C. overnight for drying. The dry bacterial cells was ground into powder. 20 mg powder was added into a 25 mL tube, and 5 mL concentrated sulfuric acid was added and heated at 90° C. for 1 h. After cooling, the mixture was diluted 100 folds with 5 mM 2% sulfuric acid at room temperature, filtered through a 0.22 μm filter (Merck Miller well, MA, USA), and 400 μL was transferred into an HPLC injection vial.

2) Determination of PHB Content

Crotonic acid was detected by an aminex HPX-87H ion-exchange column (Bio-Rad, CA, USA), and UV light signal was detected by using a UV detector (SPD-20A). It was carried out at 25° C. with 5 mM sulfuric acid as the mobile phase at a flow rate of 0.6 mL/min. Triplicate analyses were performed for each sample.

Figure 5:
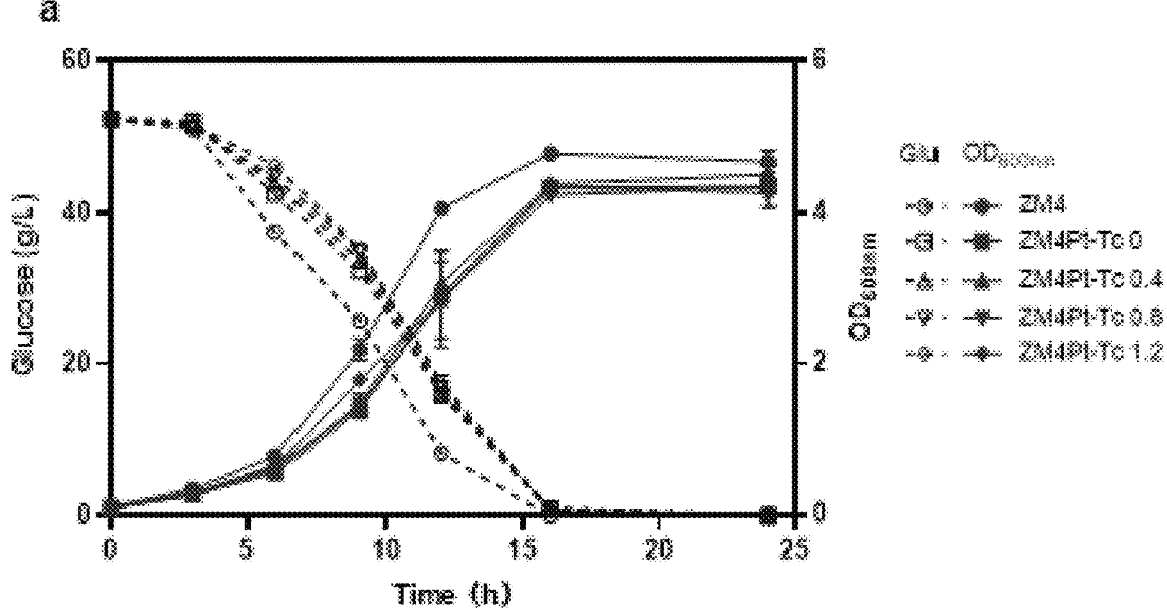
FIG. 5 illustrates a render of ZM4Pt for PHB and ethanol production with embodiments.
Figure 5:
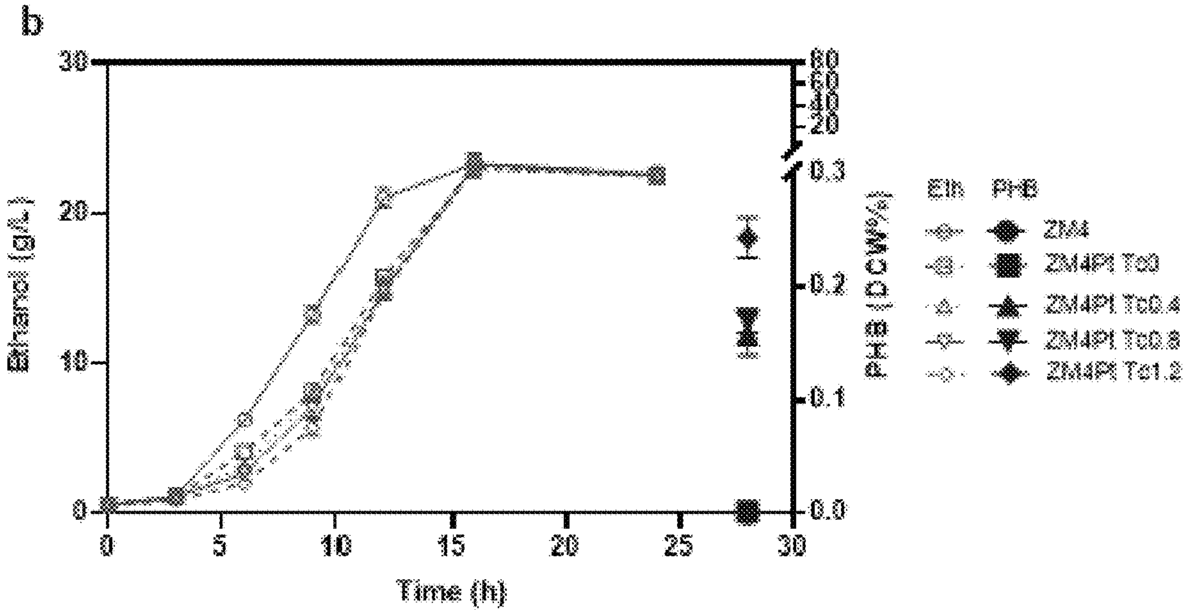

As shown in FIG. 5, the PHB content in ZM4Pt was 0.24% DCW at the concentration of 1.2 μg/mL tetracycline.

Construction and Application of Genetically Engineered Strain ZM4Pg

In some embodiments, the PHB production of genetically engineered bacteria could be enhanced by increasing the strength of the promoter and the copy number of the PHB biosynthesis genes.

In some embodiments, the recombinant plasmid pEZ-Pg was obtained by replacing the inducible promoter Ptet (SEQ ID NO:5) of the pEZ-Pt plasmid with the strong promoter Pgap (SEQ ID NO:6). The plasmid pEZ-Pg was transferred into the competent cells of ZM4 by electroporation to obtain the genetically engineered ZM4Pg. ZM4Pg was a genetically engineered strain with the strong promoter of PHB synthesis gene to increase PHB production.

1. Construction for a Recombinant Plasmid pEZ-Pg

The following primers were used for DNA amplification:

The nucleotide sequence of Pgap-CAB-F primer is:

```
                                    SEQ ID NO: 18
cttaataagttaggagaataaacatggccaccggcaaag.
```

Pgap fragment with phaCAB homology sequence was amplified by PCR using Pgap-CAB-F and phaB-R as primer pairs and pEZ-Pt plasmid as DNA template.

The Pgap fragment carrying phaCAB homologous sequence was ligated with phaCAB by overlap PCR to obtain the Pgap-phaCAB fragment.

As shown in Table 5, the Pgap-phaCAB fragment and the pEZ15A vector skeleton (containing the screening resistance gene of spectinomycin) were assembled by Gibson assembly at a molar ratio of 3:1.

TABLE 5

Gibson Assembly reaction system of Pgap-phaCAB and pEZ15A

| Reagent | Volume |
|---|---|
| Pgap-phaCAB | 0.12 pM |
| pEZ15A | 0.04 pM |
| 10 × Buffer 4 (Thermo) | 0.5 μL |
| T5 Exonuclease | 0.5 μL |
| $ddH_2O$ | To 5 μL |
| Total volume | 5 μL |

The Gibson assembly reaction products of Pgap-phaCAB and pEZ15A were placed on ice for 5 min and then transferred into *E. coli* DH5a competent cells. A plate containing 100 g/mL of spectinomycin was used for screening, and single colonies were selected by colony PCR validation (as described above; the assay reaction system is shown in Table 4) to verify the positive transformant pEZ-Pg.

2. Preparation for Genetically Engineered Bacteria ZM4Pg

The plasmids pEZ-Pg was electrotransformated into the competent cells of ZM4. After the colonies grew out, colony PCR verification was performed again (the detection method is described above, and the detection reaction system is shown in Table 4) to ensure that pEZ-Pg was transferred into ZM4, and the positive clone verified correctly was selected and named ZM4Pg.

3. Fermentation Test for Genetically Engineered Strain ZM4Pg

Figure 6:
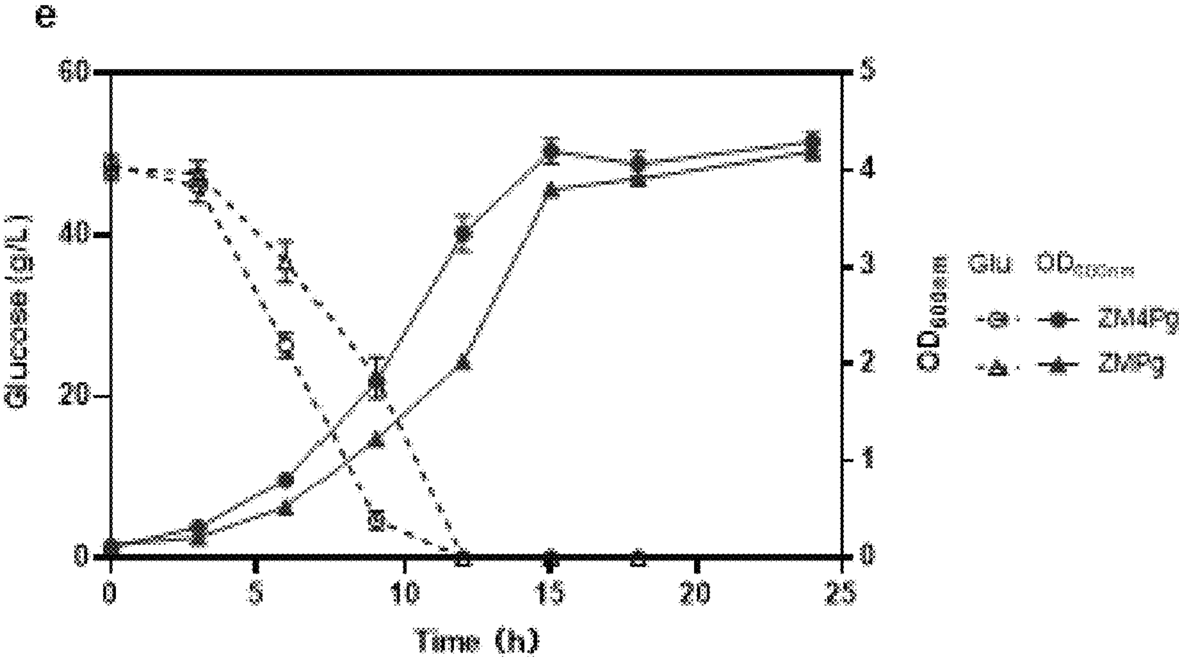
FIG. 6 illustrates a render of ZM4Pg and ZMPg for PHB and ethanol production with embodiments.
Figure 6:
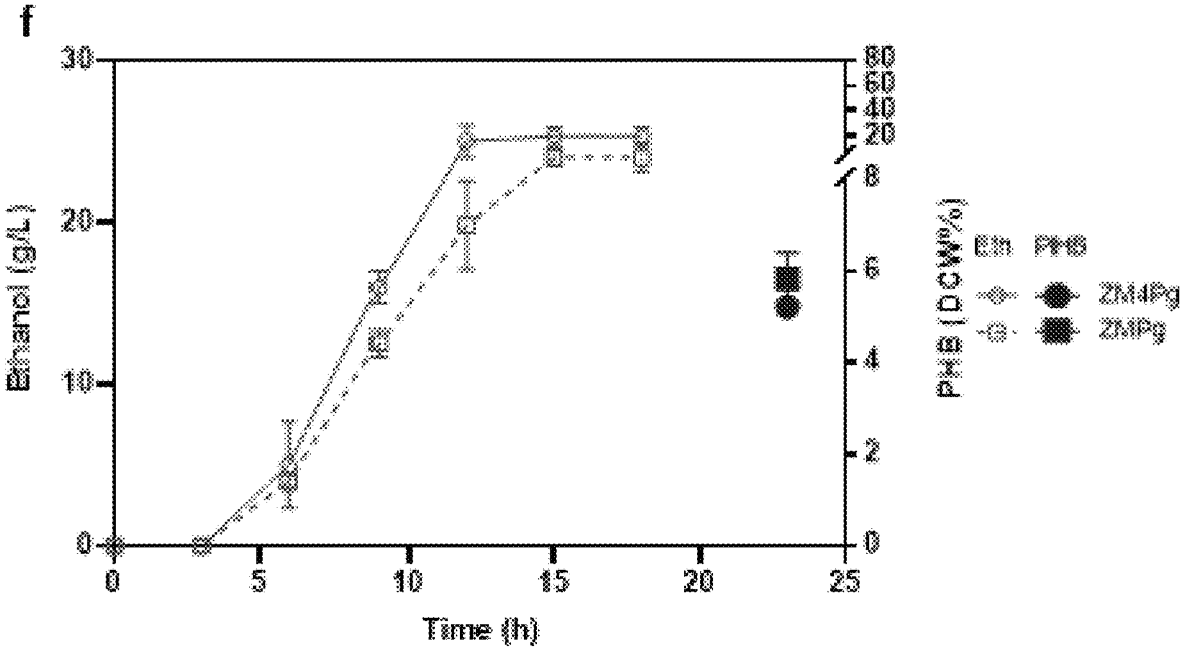

The obtained genetically engineered strain ZM4Pg was fermented in RMG5. 100 L liquid in glycerol tube of the genetically engineered bacteria ZM4Pg was inoculated into a frozen tube containing 1 mL RMG5 (with 1 μL of spectinomycin). When the bacteria grown to turbidity, it was fermented in a suitable incubator to the logarithmic stage at 30° C. The sample was inoculated into RMG5 with 80% bottling volume in a 100 mL triangular flask medium. At the beginning of fermentation, the initial value of $OD_{600nm}$ was controlled at 0.1. In the fermentation process, UV spectrophotometer was used to measure the optical density of the cell growth. The fermentation broth was collected at different time points for glucose and ethanol quantification using HPLC. The detection method was carried out for above examples. As shown in FIG. 6, the PHB yield of ZM4Pg could reach 5.22% DCW.

Construction and application of genetically engineered strains ZMPt, ZMPg, ZMPtg and ZMPgg.

Figure 7:
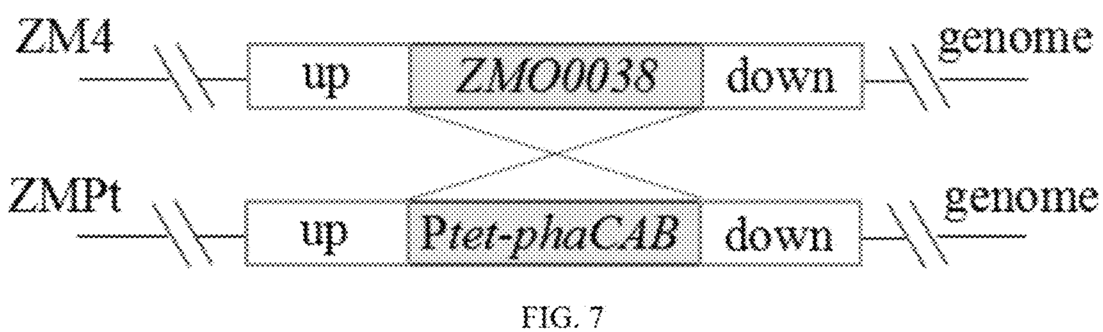
FIG. 7 illustrates Schematic of gene editing integration with embodiments.
Figure 8:
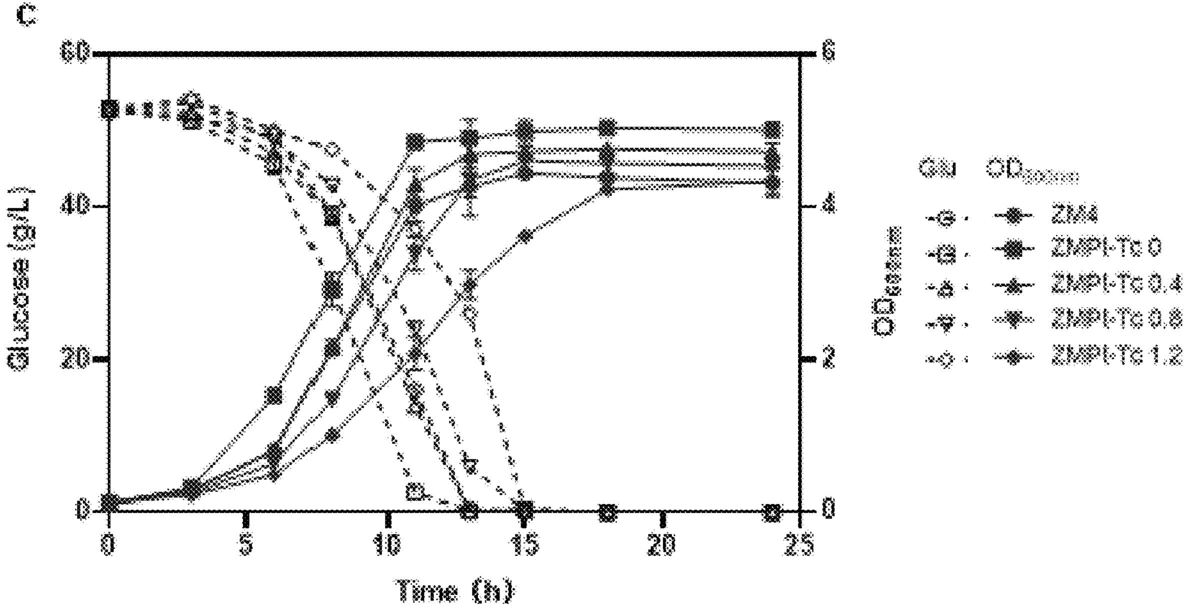
FIG. 8 illustrates a render of ZMPt for PHB and ethanol production with embodiments.
Figure 8:
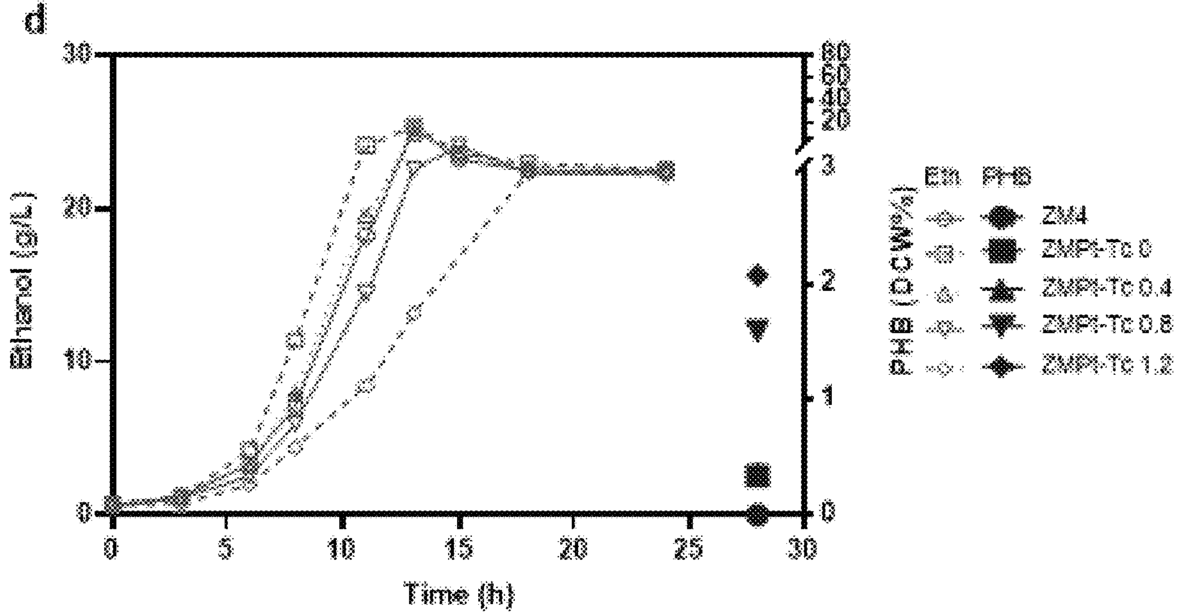

In some embodiments, as shown in FIG. 7, a genetically engineered bacteria ZMPt was constructed by integrating the Ptet-phaCAB operon fragment into the ZMO0038 gene position on the ZM4 genome with its endogenous CRISPR-Cas system. As shown in FIG. 8, at the concentration of 1.2 μg/mL tetracycline, the PHB yield of ZMPt was up to 2.07% DCW.

In one embodiment, the construction of ZMPt consisted of the following steps, and the amplification primers used for ZMO0038 gene editing were showing as follows:

1. Synthesis Primers

The nucleotide sequence of 0038-gr1-F primer is:

SEQ ID NO: 19
gaaagcgtccagcaaaatacgccttctattgatgaa.

The nucleotide sequence of 0038-gr1-R primer is:

SEQ ID NO: 20
gaacttcatcaatagaaggcgtattttgctggacgc.

The nucleotide sequence of 0038-up-F primer is:

SEQ ID NO: 21
caccagctcaccgtctgctttttgccgacaaagcg.

The nucleotide sequence of 0038-up-R primer is:

SEQ ID NO: 22
tcacgcccgacgccagacgggattagaaattttgtcg.

The nucleotide sequence of 0038-up-Ptet-F primer is:

SEQ ID NO: 23
ggcgtcgggcgtgattaagacccactttcacatttaagttgtttttctaa tc.

The nucleotide sequence of phaB-down-R primer is:

SEQ ID NO: 24
cgtctatctgaatatttaacgattaacccatatgcaagccacc.

The nucleotide sequence of 0038-down-F primer is:

SEQ ID NO: 25
tcgttaaatattcagatagacggagataataaacgggagagaggtcg.

The nucleotide sequence of 0038-down-R primer is:

SEQ ID NO: 26
gctcgagatctgatatcactcaacagatcaacc.

The nucleotide sequence of 0038-up-Pgap-F primer is:

SEQ ID NO: 27
ggcgtcgggcgtgagttcgatcaacaacccgaatcctatc.

The nucleotide sequence of CRISPR-anti-F primer is:

SEQ ID NO: 28
gtgATatCAGATCTcgagctcggtacccgggtttgac.

The nucleotide sequence of CRISPR-anti-R primer is:

SEQ ID NO: 29
gacggtgagctggtgacctgccttatctctttcccc.

The nucleotide sequence of test-0038-F primer is: tgccagcttctgttggagaaaacagg, SEQ ID NO:30.

The nucleotide sequence of test-0038-R primer is: cgcaagccaagctgcgt, SEQ ID NO:31.

The stability of strains is the key to industrial fermentation, however, plasmids are more easily losing from its host cells. Therefore, integrate the opreon into genome is effective. In this embodiment, a ZMO0038 gene editing plasmid was constructed, which was used to edit the ZMO0038 gene, and the genetic knockout of ZMO0038 would not cause negative effects on the growth of the strain.

2. Empty plasmid pL2R

A empty plasmid pL2R (construction method is described in Zheng et al., Nucleic Acids Research 47: 11461-11475) was digested overnight at 37° C. with the reaction system as shown in Table 6, and the digested products were recovered to obtain the linearized fragment of pL2R.

TABLE 6

Digestion reaction system of pL2R

| Reagent | Volume |
|---|---|
| DNA (pL2R) | 30 μL |
| Custement Buffer | 5 μL |
| BsaI | 0.5 μL |
| $ddH_2O$ | To 50 μL |
| Total volume | 50 μL |

3. ZMO0038 Guide Plasmid

For editing ZMO0038, Cas protein was booted by a guide sequence to target the position of ZMO0038. The guide sequence contains the entire 32-bp sequence of a 5'-CCC-3' PAM site of ZMO0038. Primers 0038-gr1-F (SEQ ID NO:19) and 0038-gr1-R (SEQ ID NO:20) were designed. The reagents were added to form the reaction system as shown in Table 7. The reaction mixture was heated to 95° C., anneal for 5 min, and then gradually cooled to room temperature, then the guide sequence was obtained.

TABLE 7

PCR amplification system of ZMO0038 guide sequence

| Reagent | Volume |
|---|---|
| 0038-gr1-F | 1 μL |
| 0038-gr1-R | 1 μL |
| $ddH_2O$ | To 10 μL |
| Total volume | 10 μL |

The ZMO0038 guide plasmid was constructed by ligation of the linearized fragment of pL2R and the ZMO0038 guide sequence that was obtained from a annealing reaction at 18° C. with T4 ligase. Therein, the enzymatic reaction system is shown in Table 8.

TABLE 8

Enzymatic reaction system of ZMO0038 guide sequence and pL2R

| Reagent | Volume |
|---|---|
| pL2R | 3 μL |
| ZMO0038 guide sequence | 2 μL |
| T4 Buffer | 1 μL |
| T4 DNA Ligase | 0.5 μL |
| $ddH_2O$ | To 10 μL |
| Total volume | 10 μL |

The above enzymatic reaction products were recovered, transformed into competent cells of *E. coli* DH5a strain, and spreaded on solid medium supplemented with LB and spectinomycin. And single colonies were selected for Colony PCR verification the next day. The correct transformant was selected and named as ZMO0038 guide plasmid. The validation method of the Colony PCR was performed according to above embodiments. The validation primers used in Colony PCR included 0038-gr1-F (shown in SEQ ID NO:19) and pEZ15A-R (shown in SEQ ID NO:17).

4. Synthesis for Donor Fragment of Ptet-phaCAB

The Ptet-phaCAB donor fragment was formed by Overlap PCR to connect the 500 bp upstream sequence of ZMO0038 gene, the Ptet-phaCAB operon and the 500 bp downstream sequence of ZMO0038 gene.

Therein, the 500 bp upstream sequence of ZMO0038 gene (named 0038-up stream) is as follows:

```
                                       SEQ ID NO: 32
tcacgcccgacgccagacgggattagaaattttgtcgataaacgcgccgt

gacgcaataattcttgtgggctggcctcgtggggtcttggttgtcttttg

acctttttattacgaggtagaccggaaaccgtgttcggggcagacaagcg

tccatcggatgggccgttattgtcatccaaggccataccgatttgccgtc

cgcctgtcagttcaacataaagctgtgccagcaattcggcatcgagcaag

gcgccatgtttgacgcgatggctgcggtcaataccgtagcgggtacataa

tgcgtcaagggtatgtttggcaccgggatgtttgccgcgcgcaatcgcca

aggtatcgaccattcgggtcatacaaatggtcggaaggccgcatttatcc

aattcgtaattcaaaaagccgaaatcgaaggccgcattatgggcgaccaa

aggcgacaatttgataaaggaaagcagttcttgcgctttgtcggcaaaaa

g.
```

The 500 bp downstream sequence of ZMO0038 gene (named 0038-down stream) is as follows:

```
                                       SEQ ID NO: 33
caacagatcaaccggcaatttatccacggcatcaaattcgatcggttctt

tcaggcggacaaaaaagccggagactttttttcaggctgtcgagcttgcca

tgtggtatcgcaataccatgaccaaaacctgtcgaaccgagcgtttctct

ttcatgtaaccgttcggcgataaccttggggttaattagaaattctcgcc

cagcccattgggcaacctgctggaagagtgtttttttgttagaaggattg
```

-continued

```
aaattcacctcaatcctgtccggcgcgattatatcggccagttcattcat

gtttttttcgcctttatatgcccacgattgcaaagatcgcagcatcagaca

ttttctgaaagacacagcctttcagaaaataaagtcaaaattctagcaat

attccttccggaaacgggggagaggggtcgataattctcttgaaaagagg

gagcgacctctctcccgtttattatctccgtctatctgaatatttaacg

a.
```

5. ZMO0038 Gene Editing Plasmid

The ZMO0038 guide editing plasmid was obtained by a PCR amplification that was performed by using ZMO0038 guide plasmid as the template, CRISPR-anti-F (as shown in SEQ ID NO:28) and CRISPR-anti-R (as shown in SEQ ID NO:29) as primer pairs, and the reaction system as shown in Table 9. And the amplified products were recovered.

TABLE 9

PCR amplification system of ZMO0038 guide plasmid

| Reagent | Volume |
|---|---|
| ZMO0038 guide plasmid | 3 μL |
| 2 × T5 Super PCR Mix (Tsingke) | 12.5 μL |
| 2 × T5 Primerstar (Tsingke) | 12.5 μL |
| CRISPR-anti-F | 2 μL |
| CRISPR-anti-R | 2 μL |
| $ddH_2O$ | To 50 μL |
| Total volume | 50 μL |

Then, the recombinant plasmid, ZMO0038 gene editing plasmid was obtained by Gibson assembly of the donor fragment of Ptet-phaCAB and the reverse amplified fragment of ZMO0038 guide plasmid.

In this step, the Gibson assembly reaction included:

The donor fragment of Ptet-phaCAB was mixed with the reverse amplified fragment of ZMO0038 guide plasmid in a molar ratio of 3:1, and the Gibson assembly reaction was performed in the reaction system as shown in Table 10. The reaction products obtained by Gibson assembly were left on ice for 5 minutes and then transferred into *E. coli* DH5a competent cells. A plate containing 100 μg/mL spectinomycin was used for screening, and single colonies were selected for colony PCR verification (the detection method is described above, and the detection reaction system is shown in Table 4).

ZMO0038 gene editing plasmid (Ptet-phaCAB) was obtained after verfication.

6. Transformation to Obtain ZMPt and Fermentation Test

The ZMO0038 gene editing plasmid (Ptet-phaCAB) was electroporated into ZM4, and the correct transformant was verified by colony PCR. The validation method of colony PCR was performed according to above embodiments. The primer pairs used in colony PCR validation included test-0038-F (as shown in SEQ ID NO:30) and test-0038-R (as shown in SEQ ID NO:31). If the resulting PCR product was subjected to DNA gel electrophoresis and the size of the electrophoretic band was consistent with that of Ptet-phaCAB, it was considered to be successfully edited, and the successfully edited strain was named as ZMPt. In one embodiment, the successfully edited strain was subcultured in RMG5 medium to the point where the strain could grow in RMG5 but not in the presence of RMG5 supplemented with spectinomycin to cure the editing plasmid.

The genetically engineered bacterial strain ZMPt was inoculated into 100 mL triangular flask with 80 mL RMG5 liquid medium for fermentation. The concentrations of tetracycline were 0, 0.4, 0.8, 1.2 μg/mL, and ZM4Pt was used as control. The amount of ethanol and glucose in the fermentation process and the final PHB yield were measured. The final PHB yield of ZMPt is 2.07% DCW under 1.2 μg/mL tetracycline.

In some embodiments, Pgap-phaCAB was integrated into the ZMO0038 position in the ZM4 in the same way as described above to obtain the genetically engineered strain ZMPg. As shown in FIG. 2, the PHB yield of ZMPg was up to 5.84% DCW.

Figure 9:
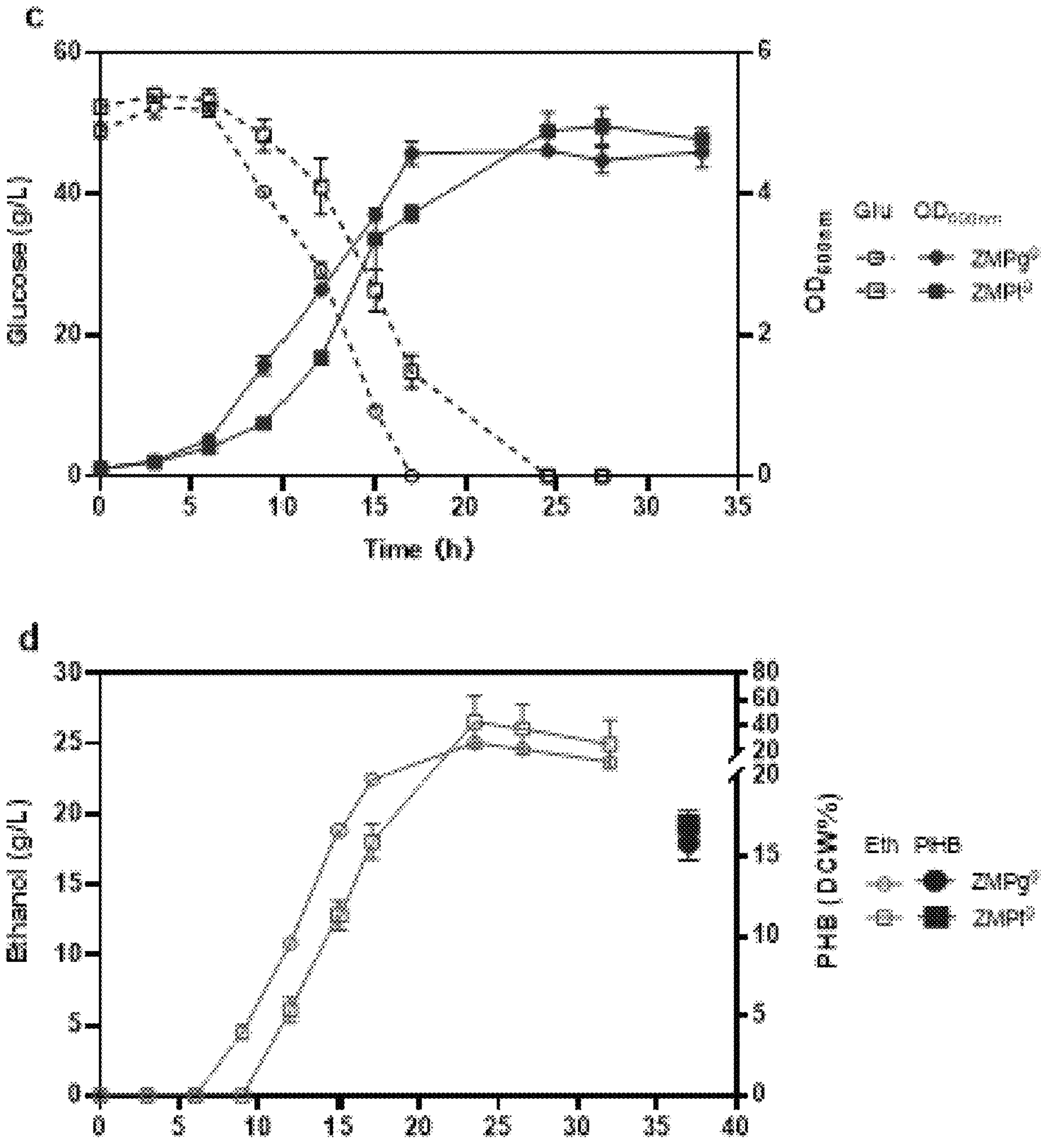
FIG. 9 illustrates a render of ZMPg$^{g}$ and ZMPt$^{g}$ for PHB and ethanol production with embodiments.

A recombinant plasmid pEZ-Pg carrying Pgap-phaCAB operon with a strong promoter was transferred into the genetically engineered strain ZMPg, resulting in a genetically engineered strain $ZMPg^g$ containing two copies of phaCAB, one at the genomic ZMO0038 gene position and one on the recombinant plasmid pEZ-Pg, respectively. As shown in FIGS. 2 and 9, the PHB yield of genetically engineered bacterial strain $ZMPg^g$ was up to 16.23% DCW.

In some embodiments, a recombinant plasmid pEZ-Pg carrying Pgap-phaCAB operon with a strong promoter was transferred into the genetically engineered strain ZMPt, producing a genetically engineered strain $ZMPt^g$ containing two copies of phaCAB, one at the genomic ZMO0038 gene position and one on the recombinant plasmid pEZ-Pg, respectively. As shown in FIGS. 2 and 9, the PHB yield of $ZMPt^g$ was up to 16.99% DCW under 1.2 μg/mL tetracycline.

Construction and application of genetically engineered bacteria ZMPtN1 and ZMPtN2

In the process of PHB accumulation, acetyl-acetyl-CoA reductase (PhaB) catalyzes the step that depends on NADPH consumption. Therefore, NADPH supply can be increased by overexpression of *Z. mobilis* endogenous genes of 6-phosphogluconate dehydrogenase (Zwf, ZMO0367) and NAD kinase (PpnK, ZMO1329), and then the PHB production can be promoted.

Figure 10:
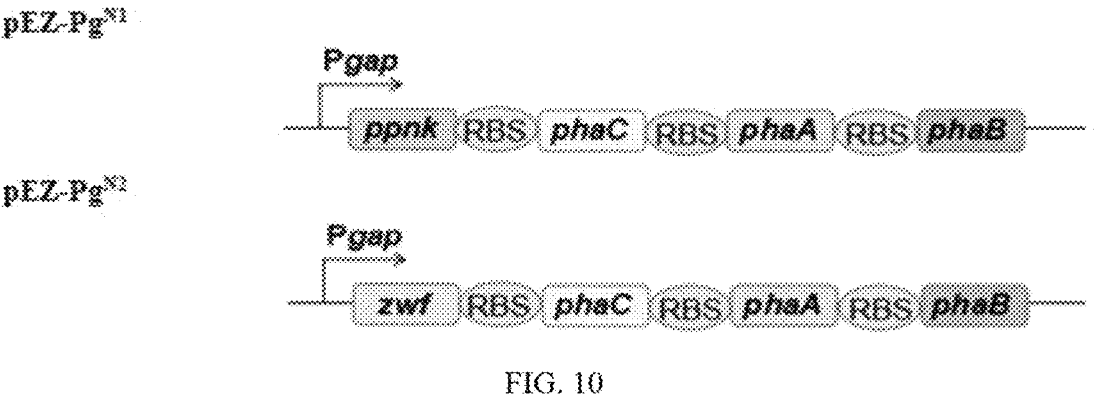
FIG. 10 illustrates the structure of recombinant plasmids pEZ-Pg$^{N1}$ and pEZ-Pg$^{N2}$.
Figure 11:
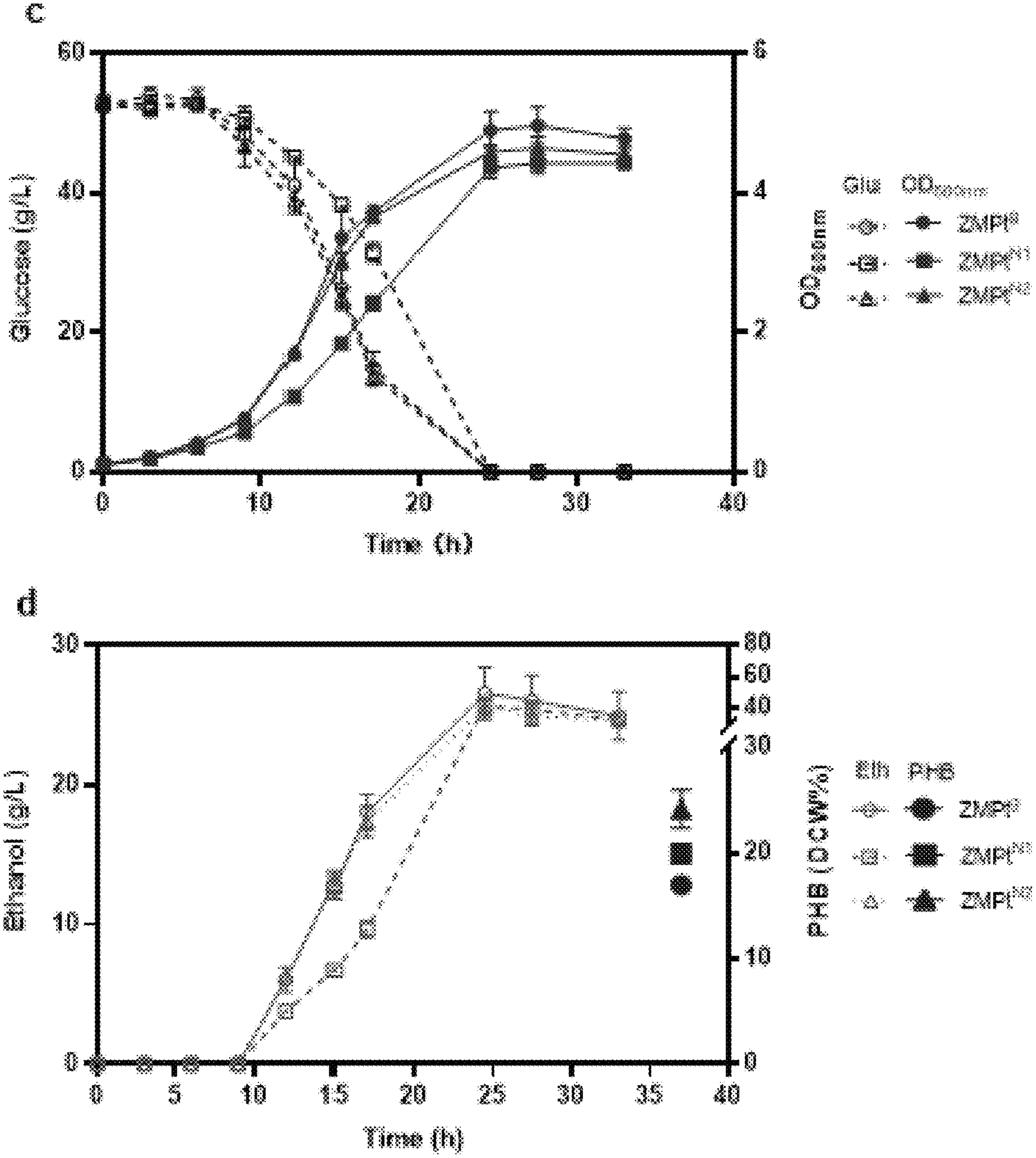
FIG. 11 illustrates renders of ZMPt$^{N1}$ and ZMPt$^{N2}$ for PHB and ethanol production with embodiments.

In this embodiment, as shown in FIG. 10, the zwf gene sequence and ppnK gene sequence were respectively ligated with the pEZ-Pg plasmid to obtain the recombinant plasmid $pEZ\text{-}Pg^{N1}$ (carrying the operon Pgap-ppnK-phaCAB) and the recombinant plasmid $pEZ\text{-}Pg^{N2}$ (carrying the operon Pgap-zwf-phaCAB). Then, the recombinant plasmids $pEZ\text{-}Pg^{N1}$ and $pEZ\text{-}Pg^{N2}$ were transformed into ZMPt cells to obtain $ZMPt^{N1}$ and $ZMPt^{N2}$, respectively. As shown in FIG. 2 and FIG. 11, the PHB yield of genetically engineered bacteria $ZMPt^{N1}$ and $ZMPt^{N2}$ were as high as 19.97% DCW and 24.22% DCW, respectively.

In one embodiment, the construction of the genetically engineered bacteria $ZMPt^{N1}$ and $ZMPt^{N2}$ specifically includes the following steps:

1. Synthetic Primers

The nucleotide sequence of PpnK-phaC-F primer is:

SEQ ID NO: 34
gttaaaaagaggagaaaggatctcccatggccaccggcaaag.

The nucleotide sequence of PpnK-R primer is:

SEQ ID NO: 35
tcctttctcctctttttaacataagcgaaattgttcgcg.

The nucleotide sequence of Zwf-F primer is: atgacaaataccgtttcgacgatg, SEQ ID NO:36.

The nucleotide sequence of Zwf-R primer is:

SEQ ID NO: 37
gagatcctttctcctcttttcagtcataccaagttactccatcac.

The nucleotide sequence of Zwf-phaC-F primer is:

SEQ ID NO: 38
aaagaggagaaaggatctcccatggccaccggcaaagg.

2. ppnK Gene Fragment

PpnK-phaC-F and PpnK-R were used as upstream and downstream primer pairs, ZM4 bacterial solution was used as the template for PCR amplification, and the PCR amplification product was recovered (according to the method of Reagent box), and 50 μL ppnK gene fragment was obtained.

3. Zwf Gene Fragment

Zwf-F and Zwf-R were used as upstream and downstream primer pairs, ZM4 bacterial solution was used as the template for PCR amplification, and the PCR amplification product was recovered (according to the method of Reagent box), and 50 μL zwf gene fragment was obtained.

4. phaCAB Fragment I and phaCAB Fragment II

Then, PpnK-phaC-F and phaB-R were used as upstream and downstream primer pairs, and pEZ-Pg plasmid was used as template to perform PCR amplification using the reaction system shown in Table 10, and the PCR amplification product was recovered to obtain phaCAB fragment I. Using Zwf-phaC-F and phaB-R as upstream and downstream primer pairs and pEZ-Pg plasmid as template, PCR amplification was performed using the reaction system shown in Table 10, and the PCR amplification product was recovered to obtain phaCAB fragment II.

TABLE 10

PCR reaction system of phaCAB fragment I and phaCAB fragment II

| Reagent | Volume |
|---|---|
| F-primer(10 μM) | 0.3 μL |
| R-primer(10 μM) | 0.3 μL |
| 2 × T5 Super PCR Mix (Tsingke) | 5 μL |
| Template | 1 μL |
| $ddH_2O$ | To 10 μL |
| Total volume | 10 μL |

5. ppnK-phaCAB Fragment and Zwf-phaCAB Fragment ppnK-phaCAB fragment was obtained by an Overlap PCR reaction of ppnK fragment and phaCAB fragment I and recovering the reaction product. zwf-phaCAB fragment was obtained by Overlap PCR reaction of zwf fragment and phaCAB fragment II and recovering the reaction product.

6. Recombinant plasmids $pEZ\text{-}Pg^{N1}$ and $pEZ\text{-}Pg^{N2}$

Recombinant plasmids $pEZ\text{-}Pg^{N1}$ and $pEZ\text{-}Pg^{N2}$ were obtained by linking the ppnK-phaCAB fragment and zwf-phaCAB fragment to the reverse-amplified pEZ-15A vector, respectively.

7. Genetically engineered strain $ZMPt^{N1}$ and $ZMPt^{N2}$

The recombinant plasmids $pEZ\text{-}Pg^{N1}$ and $pEZ\text{-}Pg^{N2}$ were transferred into ZMPt competent cells to obtain the genetically engineered strain $ZMPt^{N1}$ and $ZMPt^{N2}$, respectively.

In this embodiment, the yield of PHB and ethanol production in the fermentation broth of genetically engineered bacteria $ZMPt^{N1}$ and $ZMPt^{N2}$ were shown in FIG. 11. Finally, the yields of PHB were up to 19.97% DCW and 24.22% DCW, respectively.

Construction and Application of Genetically Engineered Bacteria ZMPtN1-EUP and ZMPtN2-EUP The ethanol utilization pathway (EUP) is a biological reaction system composed of ada gene (shown in SEQ ID NO:39) from *D. zeae* and adh2 gene (shown in SEQ ID NO:40) from *S. cerevisiae* that utilizes ethanol as substrate. The EUP pathway can convert one molecule of ethanol to acetyl-coA and produce two molecules NADHs without consuming ATP, and provides acetyl-coA dependent biochemicals in this manner. The EUP pathway was introduced into $ZMPt^{N1}$ and $ZMPt^{N2}$ to obtain $ZMPt^{N1\text{-}EUP}$ and $ZMPt^{N2\text{-}EUP}$.

In some embodiments, the construction of $ZMPt^{N1\text{-}EUP}$ and $ZMPt^{N2\text{-}EUP}$ included a step of constructing the pEZ39p plasmid, a step of constructing the recombinant plasmid pE39p-PeEUP, and a step of transferring the recombinant plasmid pE39p-PeEUP into $ZMPt^{N1}$ and $ZMPt^{N2}$, respectively. The details were showed as follows:

1. Construction for pEZ39p pEZ39P is a recombinant plasmid obtained by replacing a replicon of pEZ15A (SEQ ID NO:68) by another one that is from a endogenous plasmid from ZM4 named replicon of 39-032 (SEQ ID NO:41).

In some embodiments, pEZ39P was obtained by cloning the 39-032 replicon fragment into the pEZ15Asp vector by means of T5 Exonuclease-dependent DNA Assembly (TEDA). As shown in Table 11, the 39-032 replicon fragment was obtained by a PCR amplification using ZM4 genomic DNA as DNA amplification template, and 39-032-p-spe-F and 39-032-p-spe-R as primers.

The nucleotide sequence of 39-032-p-spe-F primer is:

SEQ ID NO: 42
ttccgtagtgagtactgaatctatcgaaaggcaaatttctttctcg.

The nucleotide sequence of 39-032-p-spe-R primer is:

SEQ ID NO: 43
agaagcggccgcgaattcagtcagaaccggcgccc.

TABLE 11

PCR reaction system of 39-032 replicon

| Reagent | Volume |
|---|---|
| 39-032-p-spe-F | 2 μL |
| 39-032-p-spe-R | 2 μL |
| 2 × T5 Super PCR Mix (Tsingke) | 12.5 μL |
| 2 × T5 Primerstar (Tsingke) | 12.5 μL |
| Template | 3 μL |
| $ddH_2O$ | To 50 μL |
| Total volume | 50 μL |

As shown in Table 12, a fragment from the pEZ15A plasmid was obtained by a PCR amplification by using pEZ15A plasmid as the DNA amplification template, and pEZ-dp-anti-F and pEZ-anti-R as primers.

The nucleotide sequence of pEZ-dp-anti-F is ctgaattcgcggccgc (SEQ ID NO:44).

The nucleotide sequence of pEZ-anti-R is attcagtactcactacggaattgc (SEQ ID NO:45).

TABLE 12

PCR reaction system of fragment from pEZ15A plasmid

| Reagent | Volume |
|---|---|
| pEZ-dp-anti-F | 2 μL |
| pEZ-anti-R | 2 μL |
| 2 × T5 Super PCR Mix (Tsingke) | 12.5 μL |
| 2 × T5 Primerstar (Tsingke) | 12.5 μL |
| Template | 3 μL |
| $ddH_2O$ | To 50 μL |
| Total volume | 50 μL |

A Gibson assembly for the 39-032 replicon fragment and the fragment from the pEZ15A plasmid shown in Table 13 was performed in a ratio of 3:1.

TABLE 13

Gibson Assembly of the 39-032 and pEZ15A

| Reagent | Volume |
|---|---|
| 39-032 replicon fragment | 0.12 pM |
| fragment from the pEZ15A plasmid | 0.04 pM |
| 10 × Buffer 4 (Thermo) | 0.5 μL |
| T5 Exonuclease | 0.5 μL |
| $ddH_2O$ | To 5 μL |
| Total volume | 5 μL |

The reaction products obtained from the Gibson assembly described above were left on ice for 5 min and then transferred into *E. coli* DH5a competent cells. The plates containing 100 μg/mL spectinomycin were used for screening, and single colonies were selected for colony PCR verification. The plasmid in the verified transformant was selected and named as pEZ39p. The validation method for this colony PCR was performed as described above, and the validation primers used for colony PCR included 39-032-seq-F (SEQ ID NO:46) and pEZ15A-R (SEQ ID NO:17).

2. Construction of Recombinant Plasmid pE39p-PeEUP

In this embodiment, a fragment of the ada-adh2 tandem gene (shown in SEQ ID NO:47) driven by the Peno promoter of the EUP pathway was inserted into pEZ39p to generate a recombinant plasmid named pE39p-PeEUP. The specific construction process of recombinant plasmid pE39p-PeEUP was showed as follows.

Spectinomycin resistance gene on pEZ39p plasmid had been replaced with kanamycin resistance gene since the constructed plasmid of the EUP pathway needs to be transferred into the strain containing the spectinomycin resistance plasmid. The recombinant plasmid pE39p-PeEUP was composed of a front reverse fragment of the resistance gene from the pEZ39p plasmid, a back reverse fragment of the resistance gene from the pEZ39p plasmid, a kanamycin resistance gene fragment and the Peno-ada-adh2 operon.

1) Front Reverse Fragment of Resistance Gene from pEZ39p Plasmid

The front reverse fragment of the resistance gene of the pEZ39p plasmid was obtained by a recovered amplification products. The pEZ39p plasmid was used as a template in a PCR amplification shown in Table 14.

TABLE 14

| PCR reaction system of front reverse fragment of resistance gene from pEZ39p | |
|---|---|
| Reagent | Volume |
| pEZ39p-F-anti-F | 2 μL |
| pEZ39p-F-anti-R | 2 μL |
| 2 × T5 Super PCR Mix (Tsingke) | 12.5 μL |
| 2 × T5 Primerstar (Tsingke) | 12.5 μL |
| pEZ39p | 3 μL |
| $ddH_2O$ | To 50 μL |
| Total volume | 50 μL |

The nucleotide sequence of pEZ39p-F-anti-F primer is: cgtcccatagatctcgagc, SEQ ID NO:48.

The nucleotide sequence of pEZ39p-F-anti-R primer is: gatgtttaactcctgaattaagccgc, SEQ ID NO:49.

2) Back Reverse Fragment of Resistance Gene from pEZ39p Plasmid

The back reverse fragment of the resistance gene of the pEZ39p plasmid was obtained by a recovered amplification products. The pEZ39p plasmid was used as a template in a PCR amplification shown in Table 15.

TABLE 15

| PCR reaction system of back reverse fragment of resistance gene from pEZ39p | |
|---|---|
| Reagent | Volume |
| pEZ39p-B-anti-F | 2 μL |
| pEZ39p-B-anti-R | 2 μL |
| 2 × T5 Super PCR Mix (Tsingke) | 12.5 μL |
| 2 × T5 Primerstar (Tsingke) | 12.5 μL |
| pEZ39p | 3 μL |
| $ddH_2O$ | To 50 μL |
| Total volume | 50 μL |

The nucleotide sequence of pEZ39p-B-anti-F primer is: tgtctaacaattcgttcaagccgacgc, SEQ ID NO:50.

The nucleotide sequence of pEZ39p-B-anti-R primer is: ctcgagagatctgatatcactctag, SEQ ID NO:51.

3) Kanamycin Resistance Gene Fragment

The kanamycin resistance gene fragment was obtained by a recovered amplification products. The ZM4 strain was used as a template in a PCR amplification shown in Table 16.

TABLE 16

| PCR reaction system of Kanamycin resistance gene fragment | |
|---|---|
| Reagent | Volume |
| Kana-F | 2 μL |
| Kana-R | 2 μL |
| 2 × T5 Super PCR Mix (Tsingke) | 12.5 μL |
| 2 × T5 Primerstar (Tsingke) | 12.5 μL |
| ZM4 | 3 μL |
| $ddH_2O$ | To 50 μL |
| Total volume | 50 μL |

The nucleotide sequence of Kana-F primer is:

SEQ ID NO: 52
gcttaattcaggagttaaacatcatgagccatattcaacgggaaacg.

The nucleotide sequence of Kana-R primer is: ttagaaaaactcatcgagcatcaaatgaaactgc, SEQ ID NO:53.

4) Construction of pEZ39p Plasmid with Kanamycin Resistance Gene

The 3' end of the reverse expansion fragment of the resistance gene in pEZ39p plasmid was designed to have a homologous sequence with the 5' end of the kanamycin gene fragment, and the 3' end of kanamycin gene fragment was designed to have a homologous sequence with the 5' end of the reverse expansion fragment of the resistance gene in the pEZ39p plasmid.

According to the principle of Overlap PCR, the front end reverse fragment of the resistance gene of the pEZ39p plasmid, the back end reverse expansion fragment of the resistance gene of the pEZ39p plasmid and the kanamycin resistance gene fragment were linked into one fragment.

The reaction steps of the Overlap PCR included:

Step 1: The reagents were mixed to form the reaction system as shown in Table 17, and PCR reaction was carried out. The PCR reaction conditions were set as follows: predenaturation at 98° C. for 3 min; ten cycles of denaturation at 98° C. for 10 s, annealing at 47° C. for 10 s, and extension at 72° C. for 40 s.

Step 2: The mixture of the Step 1 was removed, and 1.5 μL each of pEZ39p-F-anti-F and pEZ39p-B-anti-R were added as upstream and downstream primer pairs for PCR amplification. The PCR reaction conditions were set as follows: predenaturation at 98° C. for 3 min, 26 cycles of denaturation at 98° C. for 10 s, annealing at 55° C. for 10 s, and extension at 72° C. for 40 s. After the PCR was completed, the DNA electrophoresis was performed to verify the correctness, and the DNA recovery was performed after verification, thus, the pEZ39p plasmid with kanamycin resistance gene was obtained.

TABLE 17

| PCR reaction system of pEZ39p fragment with kanamycin resistance gene | |
|---|---|
| Reagent | Volume |
| front end reverse fragment of resistance gene from pEZ39p plasmid | 1 μL |
| kanamycin gene fragment | 1 μL |
| the back end reverse fragment of resistance gene from pEZ39p plasmid | 1 μL |
| 2 × T5 Super PCR Mix (Tsingke) | 12.5 μL |
| 2 × T5 Primerstar (Tsingke) | 12.5 μL |
| $ddH_2O$ | To 47 μL |
| Total volume | 47 μL |

5) Construction of Peno-Ada-Adh2 Operon

Using the reaction system shown in Table 18, PCR amplification was performed and the amplified products were recovered to obtain the Peno-ada-adh2 operon fragment.

TABLE 18

| PCR reaction system of Peno-ada-adh2 operon | |
|---|---|
| Reagent | Volume |
| Peno-F | 2 μL |
| Peno-R | 2 μL |
| 2 × T5 Super PCR Mix (Tsingke) | 12.5 μL |
| 2 × T5 Primerstar (Tsingke) | 12.5 μL |
| ZM4 strain | 3 μL |
| $ddH_2O$ | To 50 μL |
| Total volume | 50 μL |

The nucleotide sequence of Peno-F primer is:

SEQ ID NO: 54
tgtctatactccagttactcaatacgtaacaataatcagtttatcct aac.

The nucleotide sequence of Peno-R primer is: atcgaaacctttcttaaaatcttttagacgag, SEQ ID NO:55.

The 3' end of the Peno promoter is designed to share a homologous sequence with the 5' end of the ada-adh2 tandem gene.

According to the principle of Overlap PCR, the tandem gene of Peno promoter and ada-adh2 was linked into one fragment, named Peno-ada-adh2. The ada and adh2 genes were linked by RBS sequence (1381~1406 bp) to obtain ada-adh2 tandem gene fragment. Therein, ada and adh2 gene fragment were synthesized by Nanjing Genscript Company. The reaction steps of the overlap PCR included:

Step 1: The reagents were added to form a reaction system as shown in Table 20, and the PCR reaction was carried out with predenaturation at 98° C. for 3 min; ten cycles of denaturation at 98° C. for 10 s, annealing at 47° C. for 10 s, and extension at 72° C. for 20 s.

Step 2: As shown in Table 19, the mixture completed in the Step 1 was removed, and 1.5 μL each of pEZ39p-F-anti-F and pEZ39p-B-anti-R were added as upstream and downstream primer pairs for PCR amplification with pre-denaturation at 98° C. for 3 min, 26 cycles of denaturation at 98° C. for 10 s, annealing at 55° C. for 10 s, and extension at 72° C. for 20 s. After the PCR was completed, DNA electrophoresis was performed to verify the correctness of the PCR, and DNA recovery was performed to obtain the Peno-ada-adh2 fragment.

TABLE 19

PCR reaction system of Peno-ada-adh2

| Reagent | Volume |
|---|---|
| Peno | 1 μL |
| Ada-Adh2 | 1 μL |
| 2 × T5 Super PCR Mix (Tsingke) | 12.5 μL |
| 2 × T5 Primerstar (Tsingke) | 12.5 μL |
| $ddH_2O$ | To 47 μL |
| Total volume | 47 μL |

6) Gibson Assembly for pE39p-PeEUP

The Peno-ada-adh2 operon fragment was assembled at a 3:1 molar ratio with the reverse expansion vector fragment of the pEZ39p plasmid with the kanamycin resistance gene, referring to Table 20.

TABLE 20

Gibson Assembly Reaction system of pE39p-PeEUP

| Reagent | Volume |
|---|---|
| Peno-Ada-Adh2 | 0.12 pM |
| pEZ39p wih kanamycin resistance gene | 0.04 pM |
| 10 × Buffer 4 (Thermo) | 0.5 μL |
| T5 Exonuclease | 0.5 μL |
| $ddH_2O$ | To 5 μL |
| Total volume | 5 μL |

The reaction products obtained from Gibson assembly described above were left on ice for 5 min and then transferred into *E. coli* DH5a competent cells. A plate containing 200 g/mL kanamycin was used to select single colonies. Colony PCR was performed to verify the positive transformants.

The detection reaction system was shown in Table 4, wherein the primer pairs used include test 39-F and pEZ15A-R. The nucleotide sequence of test39-F primer is: ggctctaaagaaaagacagaggc, shown as SEQ ID NO:56.

3. Construction of genetically engineered bacteria $ZMPt^{N1-EUP}$ and $ZMPt^{N2-EUP}$ In this embodiment, the recombinant plasmid pE39p-PeEUP was transferred into $ZMPt^{N1}$ and $ZMPt^{N2}$ to obtain $ZMpt^{N1-EUP}$ and $ZMPt^{N2-EUP}$ respectively.

Figure 12:
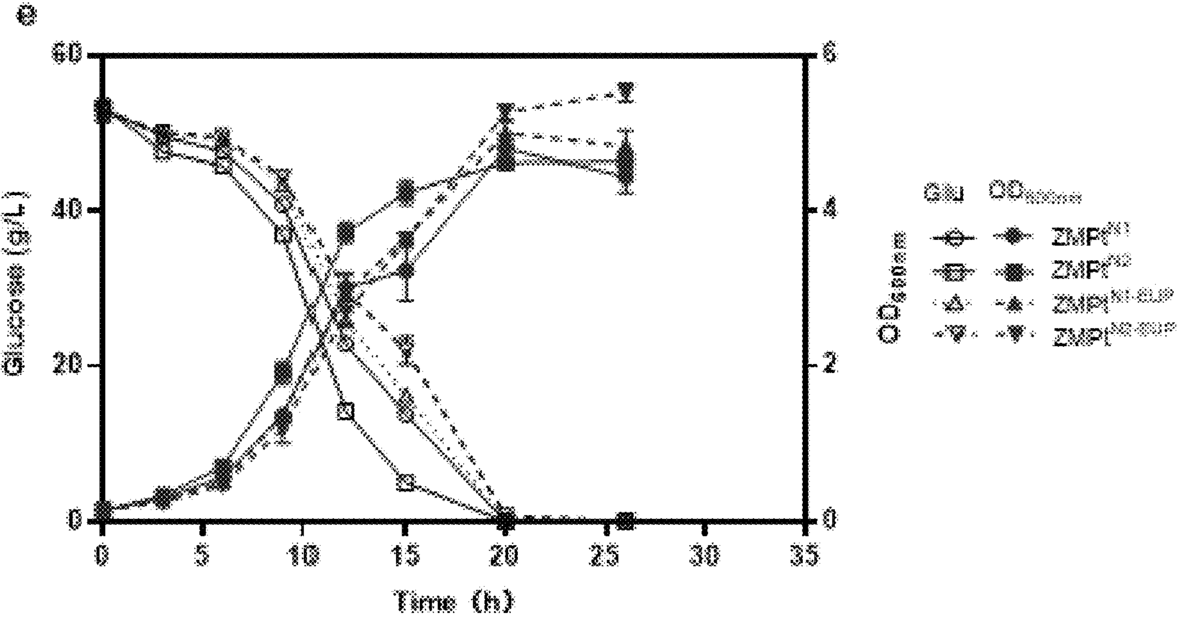
FIG. 12 illustrates renders of ZMPt$^{N1-EUP}$ and ZMPt$^{N2-EUP}$ for PHB and ethanol production with embodiments.
Figure 12:
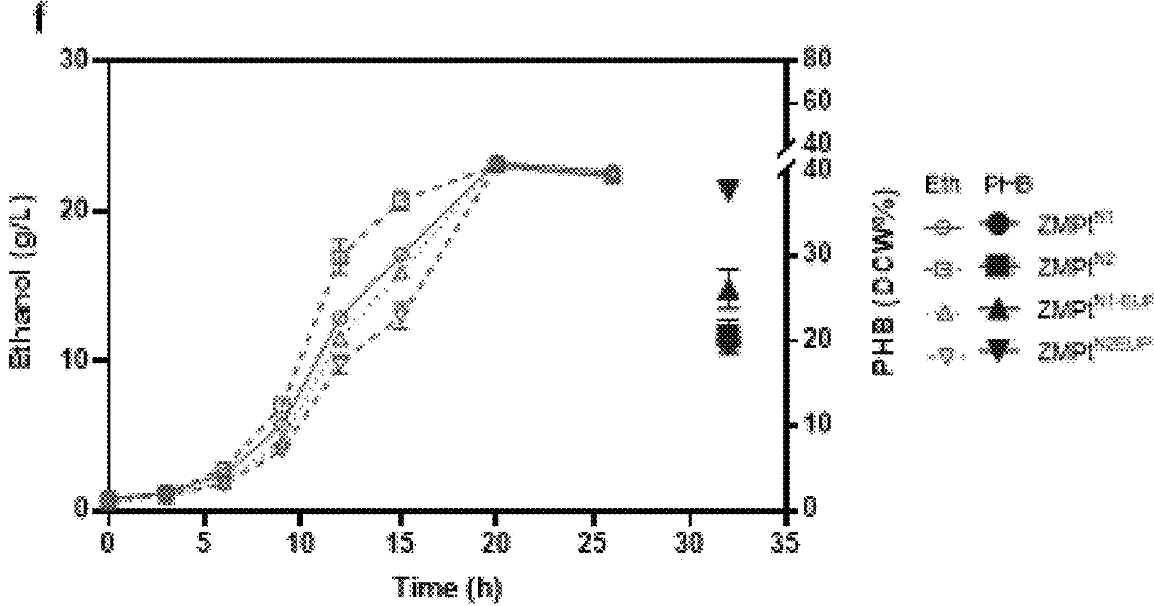

In this embodiment, the genetically engineered strain $ZMPt^{N2-EUP}$ and $ZMPt^{N2-EUP}$ were respectively inoculated into 80-mL RMG5 containing 1.2 μg/mL tetracycline in 100 mL triangular flasks, and adjusting the initial value of $OD_{600nm}$ as 0.1. And the fermentation was performed at 30° C. and 100 rpm in an incubator. Referring to FIG. 12, PHB and ethanol yields were measured at different time points during fermentation. Under these conditions, the maximum PHB yield of $ZMPt^{N1-EUP}$ and $ZMPt^{N2-EUP}$ could reach 26.15% DCW and 37.68% DCW, respectively.

Construction and Application of Genetically Engineered Strain ZMPt-Flo

ZM4 mutant ZM401 of *Z. mobilis* is self-flocculating, and a frameshift mutation was formed due to the deletion of a single nucleotide thymine in the ZM4 gene ZMO1082. This frameshift mutation integrated ZMO1082 and ZMO1083 into a fusion gene bcsA 401. The fusion gene bcsA 401 encodes the catalytic subunit of cellulose synthase, which can help cellulose synthesis and thus promote flocculation.

In this embodiment, shown as FIG. 12, the nucleotide thyminine at the corresponding position in the ZMPt gene ZMO1082 of the genetically engineered strain was deleted to obtain a frameshift mutation with a result of formation for a fusion gene bcsA 401, and a self-flocculating strain for PHB-producing named ZMPt-Flow as constructed.

In this embodiment, the amplification primers and ZMO1082 sequences required for plasmid construction were set as follows:

The nucleotide sequence of Flo-gr-F primer is:

SEQ ID NO: 57
gaaagctcttatggtggttgctgttccgctaccgct.

The nucleotide sequence of Flo-gr-R primer is:

SEQ ID NO: 58
gaacagcggtagcggaacagcaaccaccataagagc.

The nucleotide sequence of Flo-up-F primer is:

SEQ ID NO: 59
accagctcaccgtctttaactttcatatcggcgtacaagaagaag.

The nucleotide sequence of Flo-up-R primer is:

SEQ ID NO: 60
agcaaccaccataagagctgcaacggtaatcaagcaaagcaatg.

The nucleotide sequence of Flo-down-F primer is: gctcttatggtggttgctgttccg, SEQ ID NO:61.

The nucleotide sequence of Flo-down-R primer is:

```
SEQ ID NO: 62
gctcgagatctgatatcactgtcacagtcaaaaatgcagactaat

tcacc.
```

The nucleotide sequence of test-Flo-F primer is: gcgcccatcagcttttaaga, SEQ ID NO:63.

The nucleotide sequence of test-Flo-R primer is: gcgcccatcagcttttaaga, SEQ ID NO:64.

The nucleotide sequence of ZMO1082 gene is: atgcttcataaaagccgtataaaaattaaaaacacgctttctgaagctaaatatattttagagcatttgtgggattctgctct gcaatggccattgctttgcttgattaccgttgccgctcttatggtggttgctgttccgctaccgctttattatcaatgggtctatggcatttttttTat gggattgacgctgctgattga, the underlined "T" at position 181 is the nucleotide thymine to be knocked out, SEQ ID NO:65.

1. Construction of Editing Plasmids with Frameshift Mutations

1) Empty Editing Plasmid pL2R

Referring to Table 21, an empty editing plasmid pL2R (Zheng et al., *Nucleic Acids Research* 47: 1461-11475) was digested overnight at 37° C. After digesting overnight, the product was recovered to obtain a linearized fragment of pL2R.

TABLE 21

| Enymatic digestion system of pL2R | |
|---|---|
| Reagent | Volume |
| pL2R | 30 μL |
| Custement Buffer | 5 μL |
| BsaI | 0.5 μL |
| $ddH_2O$ | To 50 μL |
| Total volume | 50 μL |

2) ZMO1082 Guide Plasmid

For editing ZMO1082, Cas protein was booted by a guide sequence to target the position of ZMO1082, named ZMO1082 guide sequence. The ZMO1082 guide sequence was obtained by heating the reaction mixture to 95° C., annealing for 5 min, and then gradually cooling to room temperature. Primers Flo-gr-F and Flo-gr-R and the reactants were added to form the reaction system as shown in Table 22.

Wherein, this ZMO1082 guide sequence contains the entire 32-bp sequence of a 5'-CCC-3' PAM site of ZMO1082.

TABLE 22

| PCR reaction system of ZMO1082 guide sequence | |
|---|---|
| Reagent | Volume |
| Flo-gr-F | 1 μL |
| Flo-gr-R | 1 μL |
| $ddH_2O$ | To 10 μL |
| Total volume | 10 μL |

The ZMO1082 guide sequence was obtained by annealing reaction that was mixed with the linearized fragment of pL2R at 18° C. and ligated with T4 ligase for easy insertion and editing of ZMO1082 gene in ZM4 genome referring to Table 23.

Table 23 Enzyme-linked reaction system of ZMO1082 guide sequence and pL2R

TABLE 23

| Enzyme-linked reaction system of ZMO1082 guide sequence and pL2R | |
|---|---|
| Reagent | Volume |
| pL2R | 3 μL |
| ZMO1082 guide sequence | 2 μL |
| T4 Buffer | 1 μL |
| T4 DNA Ligase | 0.5 μL |
| $ddH_2O$ | To 10 μL |
| Total volume | 10 μL |

The enzymatic products were recovered and transformed into *E. coli* DH5a competent cells. The cells were plated on LB plus spectomycin solid medium, and single colonies were selected for colony PCR to find out the correct transformants, named ZMO1082 guide plasmid. The validation primers used in the Colony PCR included Flo-gr-F and pEZ15A-R. Referring to Table 4, The validation method of colony PCR was carried out according to the above embodiment.

3) Synthesis for a Donor Fragment

A donor fragment was formed by connecting a 600 bp middle upstream sequence of the three ZMO1081, ZMO1082 and bscA genes and a 600 bp downstream sequence of the three ZMO1081, ZMO1082 and bscA genes by overlap PCR.

The 600 bp middle upstream sequence of the three ZMO1081, ZMO1082 and bscA genes is named Flo-upstream, and its nucleotide sequence is:

```
SEQ ID NO: 66
ttaactttcatatcggcgtacaagaagaagaaatcccctt

tttgtctgtcgaaacgatggatgaattatatcaggcttcg

caggatttttcagggattactcttgcggatctaggaacgg

aaatccctaaatccagcatagcccaagaaaacattcttca

tatttccattttgtctcccaatgcaggatgtatggctctg

tttcccgaagcctttgacaagcagcattactacatcatca

ataatgaaaatgaccgctataattttcctcgtgcggcctc

tcaatttgtgcaggacatggttcaagacaatttaatcggc

atcatccgtcaggatgaagcggtgaatgaagccttgggga

aattacagcctttacatctttatgcgccgacctctgtcgc

cttaaaagattttgataactgcgcccatcagcttttaaga

atgatagaaatgaatatttcgcgtcatgcggaggtatccg

ccgatgcttcataaaagccgtataaaaattaaaaacacgc

tttctgaagctaaatatattttagagcatttgtgggattc

tgctctgcaatggccattgctttgcttgattaccgttgcc.
```

The 600 bp middle downstream sequence of the three ZMO1081, ZMO1082 and bscA genes is named Flo-downstream, and its nucleotide sequence is:

```
                                          SEQ ID NO: 67
gctcttatggtggttgctgttccgctaccgctttattatc

aatgggtctatggcatttttttatgggattgacgctgct

gattgatcgcagcccaagccattttgcctctattgttatc

tgtctttcctctattctgacttcaacccgatatatctttt

ggcgcattacgcaaacattgcgttttgaccacatcatgga

cgccgtttttggtggggttctgtttatggcagagctttat

gcatgggctattcttatattagggttgttccagattttat

ggccgatgcagcgtcctgttgtcccgttatcaggcgagga

tgaagagttacctacagttgatgtctttattccgacttat

aacgaaagcatggaaatcgttcaaaataccgttttcgcgg

ctttgggaatggattatccaaaagaccgctttaacgttta

tctgttggatgatggtcatcgagaagaattccgcctttt

gcagaagaggcgggatgccattatttaacccgtaatgata

atctgaatgccaaggcgggtaacctaaatgcggccttgaa

aaagaccaaaggtgaattagtctgcattttgactgtgac.
```

4) Construction of Gene Editing Plasmids for Frameshift Mutations

Referring to Table 24, the gene editing plasmids for frameshift mutations was obtained by PCR amplification with ZMO1082 guide plasmid as the template and CRISPR-anti-F and CRISPR-anti-R as primers, and the amplification products were recovered.

TABLE 24

PCR reaction of gene editing plasmids for frameshift mutations

| Reagent | Volume |
|---|---|
| ZMO1082 guide plasmid | 3 μL |
| 2 × T5 Super PCR Mix (Tsingke) | 12.5 μL |
| 2 × T5 Primerstar (Tsingke) | 12.5 μL |
| CRISPR-anti-F | 2 μL |
| CRISPR-anti-R | 2 μL |
| $ddH_2O$ | To 50 μL |
| Total volume | 50 μL |

The frameshift mutation gene editing plasmid was obtained by a Gibson assembly of the reverse amplification fragment from the donor fragment and the ZMO1082 guide plasmid.

In this step, the Gibson assembly reaction included:

Referring to Table 25, the donor fragment and the reverse amplified fragment of ZMO082 guide plasmid which contains a kanamycin screening resistance gene, were assembled at a mole ratio of 3:1.

TABLE 25

Gibson Assembly of frameshift mutation gene editing plasmid

| Reagent | Volume |
|---|---|
| donor fragment | 0.12 pM |
| reverse amplified fragment of ZMO1082 guide plasmid | 0.04 pM |
| 10 × Buffer 4 (Thermo) | 0.5 μL |
| T5 Exonuclease | 0.5 μL |
| $ddH_2O$ | To 5 μL |
| Total volume | 5 μL |

The Gibson assembly reaction products were left on ice for 5 min and then transferred into *E. coli* DH5a competent cells. Plates containing 200 μg/mL kanamycin were used to select single colonies, and colony PCR was performed to verify the positive transformants. Therein, colony PCR validation was performed according to the above embodiments. After the verified positive transformants were cultured, the cells were collected and the plasmids were extracted to obtain the frameshift mutation gene editing plasmids.

2. Construction of Genetically Engineered Strain ZMPt-Flo

The frameshift mutation editing plasmid was transformed into the genetically engineered strain ZMPt. The PCR products were sent to Tsingke Biotechnology Co., Ltd. for Sanger sequencing verfication. The flocculating strain ZMPt-Flo was obtained by subculturing the edited strain until it could grow in RMG5 but not in RMG5 with spectinomycin, and the gene-editing plasmids was cured.

Construction and Application of Genetically Engineered Strain ZMPt-FloN2

The process for acetoacetyl-coA reductase (PhaB) catalyzing is dependent on NADPH consumption during PHB accumulation. Therefore, overexpression of gene (zwf) encoding the endogenous glucose-6-phosphate dehydrogenase could enhance NADPH supply and promote PHB production in the fermentation.

Figure 15:
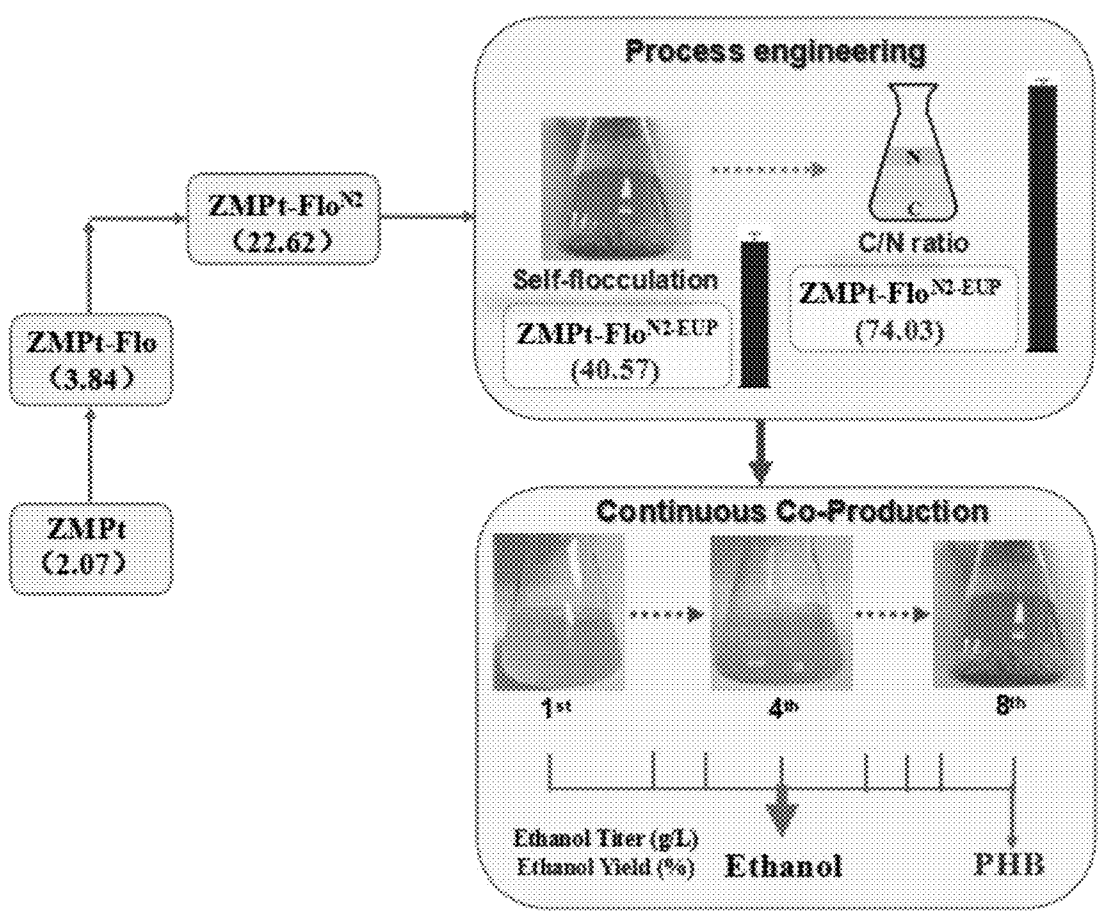
FIG. 15 illustrates the construction, process optimization of PHB, alcohol producing for self-flocculating strains of *Z. mobilis* ZM4, and operation flow chart of ethanol continuous fermentation and PHB production of self-flocculation strains with embodiments.

This embodiment combined a strong promoter-driven overexpression cofactor supply related gene with a phaCAB fragment in series to obtain the Pgap-zwf-phaCAB operon, and the Pgap-zwf-phaCAB operon was inserted into pEZ-15A, and the recombinant plasmid pEZ-Pg$^{N2}$ was obtained. Then, the recombinant plasmid pEZ-Pg$^{N2}$ was transferred into ZMPt-Flo cells to obtain ZMPt-Flo$^{N2}$. As shown in FIG. 13 and FIG. 15, the PHB yield of the ZMPt-Flo$^{N2}$ could reach to 22.62% DCW.

Construction and Application of the Genetically Engineered Strain ZMPt-FloN2-EUP The ethanol utilization pathway (EUP) is a bioreaction system composed of the ada gene (SEQ ID NO:39) from *Di. zeae* and adh2 gene (SEQ ID NO:40) from *S. cerevisiae* that utilizes ethanol. The EUP pathway can provide acetyl-coA dependent biochemicals by converting one molecule of ethanol to acetyl-coA and producing two molecules of NADHs without consuming ATP. By introducing the EUP pathway into ZM4 strain through gene editing and recombination, the genetically engineered strain ZMPt-Flo$^{N2\text{-}EUP}$ was obtained, which could not only self-flocculated, but also produced ethanol and PHB simultaneously.

In this embodiment, the construction steps of the genetically engineered strain ZMPt-Flo$^{N2\text{-}EUP}$ included the construction of the pEZ39p plasmid, the construction of the recombinant plasmid pE39p-PeEUP, and the transfer of the recombinant plasmid pE39p-PeEUP into ZMPt-Flo$^{N2}$, respectively. The construction process was performed with reference to the above embodiments.

In this embodiment, the genetically engineered strain ZMPt-Flo$^{N2-EUP}$ was fermented in 80 mL RMG5 medium in a 100 mL triangular flask with 1.2 μg/mL tetracycline at 30° C. with 100 rpm, and the initial $OD_{600nm}$ was 0.1. The PHB yield of ZMPt-Flo$^{N2-EUP}$ was up to 40.57% DCW.

Optimization of Fermentation Conditions

Many studies have found that PHB can be accumulated in microorganisms under high C/N ratio or N limitation.

In this embodiment, the PHB yields of ZMPt$^{N1-EUP}$ and ZMPt-Flo$^{N2-EUP}$ were optimized with different ratios of carbon and nitrogen sources. In fermentation experiments with different C/N ratios, four different ratios were selected with glucose and yeast extracts at 10:1 with 50/5 (50 g/L glucose and 5 g/L yeast extract) and 20/2 (20 g/L glucose and 2 g/L yeast extract), and 5:1 with 50/10 (50 g/L glucose and 10 g/L yeast extract) and 20/4 (20 g/L glucose and 4 g/L yeast extract), respectively. The initial $OD_{600nm}$ was controlled at 0.1. The cells were collected to measure the PHB content and the changes of glucose and ethanol during the fermentation process.

Figure 14:
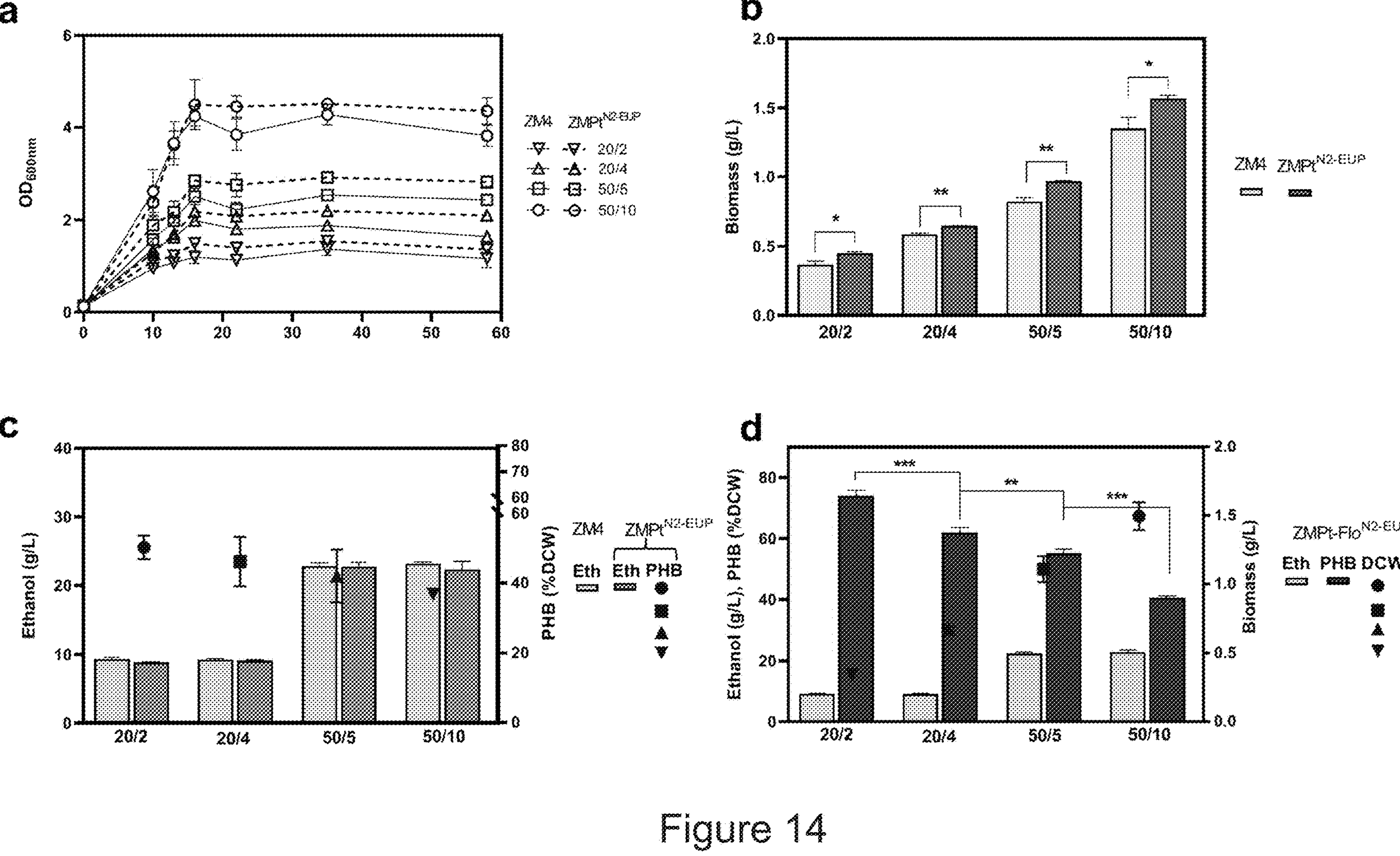
FIG. 14 illustrates a plot of PHB and alcohol producing in recombinant strain ZMPt$^{N2-EUP}$ and control ZM4 and the self-flocculation strain ZMPt-Flo$^{N2-EUP}$ under different C/N ratios with embodiments.

Referring to FIG. 14, the genetically engineered strain ZMPt-Flo$^{N2-EUP}$ accumulated PHB up to 74.03±1.81% DCW at a C/N ratio of 20/2.

FIG. 15 shows the construction of the genetically engineered strain ZMPt-Flo$^{N2-EUP}$ and the operation process of continuous fermentation for co-production of PHB and ethanol.

Referring to FIG. 15, the PHB, glucose and ethanol contents were tested. The PHB yield could be accumulated up to 40.57% DCW. After adjusting the ratio of carbon and nitrogen sources, the yield of PHB further reached to 74.03% DCW at a C/N ratio of 20/2 (20 g/L glucose and 2 g/L yeast extract).

Continuous fermentation test

In an embodiment, as shown in FIG. 16, ZMPt-Flo$^{N2-EUP}$ was used for continuous fermentation with 150 g/L glucose. ZMPt-Flo$^{N2-EUP}$ strain was inoculated into RMG15 medium (glucose 150 g/L, yeast extract 10 g/L, potassium dihydrogen phosphate 2 g/L) with the initial $OD_{600nm}$ of 0.3 at 30° C. and 100 rpm. The glucose consumption was detected. When all the glucose has been consumed, the supernatant of the medium was poured with the sediment left in the flask. Then, fresh RMG15 medium with 100 μg/mL spectomycin, 100 μg/mL kanamycin and 1.2 μg/mL tetracycline was added.

In an embodiment, an experiment for continuous fermentation using the recombinant PHB producer strain ZMPt-Flo$^{N2-EUP}$ had been exhibited the advantage of co-production of ethanol and PHB.

As shown in FIG. 16, the genetically engineered strain ZMPt-Flo$^{N2-EUP}$ cells could consume all sugar with similar ethanol fermentation performance without sacrificing ethanol titer in each 8 cycles used in this disclosure, even after the last cycle. Therefore, fermentation could be carried out without seed culture inoculation for each cycle, which would save time and the operation cost of seed culture preparation. In addition, more cell biomass had been accumulated after each cycle, which not only accelerated the fermentation progress, but also increased the final PHB amount. After each cycle, ethanol could be separated from water in the fermentation broth using membrane separation technique, and water could be recycled for media preparation in next cycle, which would help save water and preserve the environment. After finishing fermentation, which probably could last for a long period of times than 8 cycles used in this study, cell biomass could then be used for PHB production.

The above is only the preferred embodiments of this disclosure and is not intended to limit this disclosure. Any modification, equivalent replacement, improvement, etc., made within the spirit and principle of this disclosure shall be included in the scope of this disclosure.

What is claimed is:

1. An application of genetically engineered strain in simultaneous production of ethanol and poly-p-hydroxybutyric PHB, wherein, the genetically engineered strain is selected from the group consisting of the strains named ZMPtN1-EUP, ZMPtN2-EUP, or ZMPt-FloN2-EUP;

the strain ZMPtN1-EUP is obtained by transferring plasmid pE39p-PeEUP into strain ZMPtN1, and the ZMPtN1 is obtained by transferring plasmid pEZ-PgN1 into strain ZMPt; the ZMPtN2-EUP strain is obtained by transferring the pE39p-PeEUP plasmid into strain ZMPtN2, and the ZMPtN2 is obtained by transferring plasmid pEZ-PgN2 into strain ZMPt;

the ZMPt-FloN2-EUP strain is obtained by transferring the pE39p-PeEUP plasmid into a strain named ZMPt-FloN2, and the ZMPt-FloN2 is obtained by transferring the pEZ-PgN2 plasmid into a strain named ZMPt-Flo;

the ZMPt is obtained by replacing the ZMO0038 gene of the *Zymomomonas mobilis* (*Z. mobilis*) ZM4 strain genome with an Ptet-phaCAB operon;

the ZMPt-Flo is obtained by replacing the genome ZMO0038 of *Z. mobilis* ZM4 strain genome with the Ptet-phaCAB operon and knocking out the 181th nucleotide of ZMO1082 gene of *Z. mobilis* ZM4 strain genome with thymidine;

a plasmid named pEZ-Pt is a recombinant plasmid prepared by linking the Ptet-phaCAB operon to the pEZ15A vector;

the pEZ-Pg is a recombinant plasmid obtained by replacing the inducible promoter Ptet of plasmid pEZ-Pt with a strong promoter Pgap;

the pEZ-PgN1 is a recombinant plasmid obtained by linking the gene ZMO1329 with a plasmid pEZ-Pg;

the pEZ-PgN2 is a recombinant plasmid obtained by linking the gene ZM00367 with the plasmid pEZ-Pg;

the pE39p-PeEUP is a recombinant plasmid obtained by constructing the ada and adh2 genes connected by ribosome binding site (RBS) sequence into a shuttle vector pEZ39p, and the pEZ39p is a recombinant plasmid obtained by replacing the replicon of a plasmid pEZ15A with the replicon from a endogenous plasmid 39-032 in *Z. mobilis*ZM4;

the Ptet-phaCAB has a nucleotide sequence formed by sequential connection of Ptet, phaC, RBS, phaA, and phaB elements, and the nucleotide sequences of phaC, phaA, and phaB are sequentially shown as SEQ ID NO:1 to 3; the nucleotide sequence of the RBS is shown as SEQ ID NO:4; the nucleotide sequence of ada and adh2 are shown as SEQ ID NO: 39 and SEQ ID NO: 40, respectively; the nucleotide sequence of the replicon of 39-032 from *Z. mobilis* ZM4 shown as SEQ ID NO:41;

the pEZ39p is constructed as follows 1)~2):

1) a PCR is presented by amplifying a fragment from the replicon of 39-032 from *Z. mobilis* ZM4, with *Z. mobilis* ZM4 strain as the DNA template, 39-032-p-spe-F and 39-032-p-spe-R as primers; the nucleotide sequence of 39-032-p-spe-F is shown as SEQ ID NO:42, and the nucleotide sequence of 39-032-p-spe-R is shown as SEQ ID NO:43;

2) a PCR is presented by amplifying a reverse fragment from pEZ15A, with the pEZ15A used as the DNA amplification template, and pEZ-dp-anti-F and pEZ-anti-R used as primers; the nucleotide sequence of pEZ-dp-anti-F is shown as SEQ ID NO: 44, the nucleotide sequence of pEZ-anti-R is shown as SEQ ID NO: 45:

the described strains ZMPtN1-EUP and ZMPtN2-EUP are respectively inoculated into a 100 ml triangular flask containing 80 mL RMG5 medium supplemented with tetracycline inducer at a concentration of 1.2 μg/mL to an initial OD600nm of 0.1; and then fermented at 30° C. and 100 rpm;

the described strains ZMPt-FloN2-EUP is inoculated into a 100-ml triangular flask containing 80 mL RMG5 medium supplemented with tetracycline inducer at a concentration of 1.2 μg/ml to an initial OD600nm of 0.1; and then fermented at 30° C. and 100 rpm.

2. The application of claim 1, where the pEZ-PgN2 plasmid is constructed by the following:

amplifying the phaCAB fragment from the Ptet-phaCAB operon using Zwf-phaC F and phaB R as primers;

ligating a fragment named Zwf from ZMO0367 gene with phaCAB fragment to obtain Zwf-phaCAB fragment;

ligating the Zwf-phaCAB fragment with the Pgap promoter to form the Pgap-Zwf-phaCAB operon; and assembling the Pgap-Zwf-phaCAB operon with the reverse fragment from pEZ15A to obtain the pEZ-PgN2;

wherein, the nucleotide sequence of Zwf-phaC-F primer is shown as SEQ ID NO: 38; the nucleotide sequence of phaB-R primer is shown as SEQ ID NO: 13.

3. The application of claim 1, where the of the pEZ-Pg plasmid is constructed by the following:

amplifying to obtain the Pgap promoter and a phaCAB fragment possess a homology arm with the Pgap by PCR, which was performed by using pEZ-P-t plasmid as DNA template, and Pgap-CAB-F and phaB-R as primers;

ligating the Pgap promoter and the phaCAB fragment possess a homology arm with the Pgap to obtain the Pgap-phaCAB fragment by an Overlap PCR;

and assembling the Pgap-phaCAB fragment and the pEZ15A vector backbone containing spectinomycin resistance gene at a molar ratio of 3:1 to obtain the pEZ-Pg plasmid by Gibson assembly reaction;

wherein the nucleotide sequence of Pgap-CAB-F primer is shown as SEQ ID NO: 18;

the nucleotide sequence of phaB-R primer is shown as SEQ ID NO:13;

the pEZ-Pt plasmid is prepared by linking the Ptet-phaCAB operon to the vector of pEZ15A.

4. The appliacation of claim 1, wherein, the tetracycline is used to induce the production of ethanol and PHB during the cultivation process of strain ZMPtN1-EUP, ZMPtN2-EUP, or ZMPt-FloN2-EUP.

5. The application of claim 1, wherein, the medium used for fermentation production is RMG5 medium with a C/N ratio of 5~10:1.

6. The application of claim 1, further comprising a cyclic fermentation performed in strain ZMpt-FloN2-EUP to produce ethanol and PHB simultaneously.

* * * * *